(12) United States Patent
LaPosta et al.

(10) Patent No.: US 6,709,658 B1
(45) Date of Patent: Mar. 23, 2004

(54) PNEUMOCOCCAL VACCINES FORMULATED WITH INTERLEUKIN-12

(75) Inventors: Vincent J. LaPosta, Pittsford, NY (US); John H. Eldridge, Fairport, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 09/248,195

(22) Filed: Feb. 10, 1999

Related U.S. Application Data

(60) Provisional application No. 60/074,528, filed on Feb. 12, 1998.

(51) Int. Cl.[7] ............................................. A61K 39/385
(52) U.S. Cl. ................................ 424/195.11; 424/184.1; 424/198.1; 424/193.1; 424/244.1; 424/85.2; 514/2; 514/8; 514/12; 514/54; 514/885
(58) Field of Search ......................... 424/184.1, 198.1, 424/193.1, 244.1, 195.11, 85.2; 514/2, 8, 12, 54, 885

(56) References Cited

U.S. PATENT DOCUMENTS

| | | | | |
|---|---|---|---|---|
| 4,711,779 A | * | 12/1987 | Porro et al. | |
| 4,761,283 A | * | 8/1988 | Anderson | |
| 5,723,127 A | * | 3/1998 | Scott et al. | |
| 6,303,114 B1 | * | 10/2001 | Metzger et al. | |

OTHER PUBLICATIONS

Metzger etal. Ann. NY. Acad. Sci. 1996 795:100–113.*
Metzger et al. Eur. J. Immunol. 1997. 27:1958–1965.*

* cited by examiner

*Primary Examiner*—Jennifer E. Graser
(74) *Attorney, Agent, or Firm*—Alan M. Gordon

(57) ABSTRACT

This invention pertains to vaccine compositions comprising a mixture of antigen, such as a pneumococcal or meningococcal antigen, and interleukin IL-12, which may be adsorbed onto a mineral in suspension. The pneumococcal or meningococcal antigen may be conjugated to a carrier molecule. These vaccine compositions modulate the protective immune response to the antigen.

24 Claims, No Drawings

PNEUMOCOCCAL VACCINES FORMULATED WITH INTERLEUKIN-12

This application claims priority from U.S. Provisional Patent Application Serial No. 60/074,528, filed Feb. 12, 1998.

BACKGROUND OF THE INVENTION

The immune system uses many mechanisms for attacking pathogens; however, not all of these mechanisms are necessarily activated after immunization. Protective immunity induced by vaccination is dependent on the capacity of the vaccine to elicit the appropriate immune response to resist or eliminate the pathogen. Depending on the pathogen, this may require a cell-mediated and/or humoral immune response.

The current paradigm for the role of helper T cells in the immune response is that they can be separated into subsets on the basis of the cytokines they produce, and that the distinct cytokine profile observed in these cells determines their function. This T cell model includes two major subsets: TH-1 cells that produce IL-2 and interferon $\gamma$(IFN-$\gamma$) which augment both cellular and humoral immune responses, and TH-2 cells that produce IL-4, IL-5 and IL-10 which augment humoral immune responses (Mosmann et al., *J. Immunol.* 126:2348 (1986)). It is often desirable to enhance the immunogenic potency of an antigen in order to obtain a stronger immune response in the organism being immunized and co strengthen host resistance to the antigen-bearing agent. A substance that enhances the immunogenicity of an antigen with which it is administered is known as an adjuvant. For example, certain lymphokines have been shown to have adjuvant activity, thereby enhancing the immune response to an antigen (Nencioni et al., *J. Immunol.* 139:800–804 (1987); EP285441 to Howard et al.).

SUMMARY OF THE INVENTION

This invention pertains to vaccine compositions comprising a mixture of one or more pneumococcal or meningococcal antigens, the interleukin IL-12 and a mineral in suspension. The IL-12 can be either adsorbed onto the mineral suspension or simply mixed therewith. In a particular embodiment of the invention, the IL-12 is adsorbed onto a mineral suspension such as alum (e.g., aluminum hydroxide or aluminum phosphate). These vaccine compositions modulate the protective immune response to the antigen; that is, the vaccine composition is capable of quantitatively and qualitatively improving the vaccinated host's antibody response, and quantitatively increasing cell-mediated immunity for a protective response to a pathogen. In a particular embodiment of the invention, the antigen is a pneumococcal or meningococcal antigen; the antigens are optionally conjugated to a carrier molecule, such as in a pneumococcal or meningococcal glycoconjugate.

Studies described herein show that IL-12 can modify the humoral response of mice immunized with pneumococcal and meningococcal glycoconjugate vaccines formulated with aluminum phosphate (AlPO$_4$) The particular pneumococcal polysaccharide serotypes exemplified herein are serotypes 1, 4, 5, 6B, 9V, 14, 18C, 19F, and 23F, (Pn1, Pn4, Pn5, Pn6B, Pn9V, Pn14, Pn18C, Pn19F, Pn23F), and the meningococcal polysaccharide is type C (Men C). These serotypes, however, are not to be construed to limit the scope of the invention, as other pneumococcal and meningococcal serotypes are also suitable for use herein. Moreover, it will be apparent to the skilled artisan that conjugation to a carrier molecule, such as the CRM$_{197}$ protein exemplified herein, is optional, depending upon the immunogenicity of the selected pneumococcal or meningococcal antigen.

Doses of IL-12 ranging from about 8 ng to about 1,000 ng increased the IgG1, IgG2a, IgG2b and IgG3 response to alum-adsorbed Pn14 or Pn6B. In addition they increased the IgG2a response to Pn4 and Pn9V. Doses of IL-12 of about 5,000 ng markedly reduced the overall IgG titers to Pn14, and especially the IgG1 and IgG2b titers.

The invention also pertains to methods for preparing an immunogenic composition or a vaccine composition comprising a mixture of antigen and IL-12 with a mineral in suspension. In particular, the IL-12 is adsorbed onto the mineral suspension. The invention also pertains to methods for eliciting or increasing a vaccinee's IFN-$\gamma$-producing T cells and complement-fixing IgG antibodies for a protective immune response, comprising administering to a mammalian, e.g., human or primate, host an effective amount of a vaccine composition comprising a mixture of antigen, IL-12 and a mineral in suspension in a physiologically acceptable solution. In particular, the IL-12 is adsorbed onto the mineral suspension.

DETAILED DESCRIPTION OF THE INVENTION

Work described herein reveals the ability of IL-12 to increase the immune response to alum-based pneumococcal vaccines, particularly serotype 14 and serotype 6B pneumococcal glycoconjugate vaccines, and meningococcal vaccines, particularly type C, to increase the proportion of complement-fixing IgG2a and IgG2b antibodies. As described herein, PnPs-14-CRM$_{197}$ vaccine comprises a serotype 14 pneumococcal polysaccharide conjugated to a non-toxic mutant of diphtheria toxoid (cross-reacting material) designated CRM$_{197}$, and PnPs6B-CRM$_{197}$ vaccine comprises a serotype 6B pneumococcal polysaccharide conjugated to CRM$_{197}$. IL-12 was compared to MPL® (3-O-deacylated monophosphoryl lipid A; RIBI ImmunoChem Research, Inc., Hamitton, Mont.), which in mice is a potent adjuvant for pneumococcal vaccines. In a separate experiment conducted in Balb/c mice, the effect of IL-12 on the cytokine profile of the CRM-specific T cells induced by the exemplary conjugate vaccines on alum was examined.

IL-12 is produced by a variety of antigen-presenting cells, principally macrophaqes and monocytes. It is a critical element in the induction of TH-1 cells from naive T cells. Production of IL-12 or the ability to respond to it has been shown to be critical in the development of protective TH-1-like responses, for example, during parasitic infections, most notably Leishmaniasis (Scott et al., U.S. Pat. No. 5,571,55). The effects of IL-12 are mediated by IFN-$\gamma$ produced by NK cells and T helper cells. Interleukin-12 (IL-12), originally called natural killer cell stimulatory factor, is a heterodimeric cytokine (Kobayashi et al., *J. Exp. Med.* 170:827 (1989)). The expression and isolation of IL-12 protein in recombinant host cells is described in International Patent Application WO 90/05147, published May 17, 1990.

The studies described herein reveal the utility of IL-12 as an adjuvant in a pneumococcal or meningococcal vaccine, and particularly a pneumococcal or meningococcal glycoconjugate vaccine. Accordingly, this invention pertains to vaccine compositions comprising a mixture of such an antigen, IL-12 and a mineral in suspension. In a particular embodiment of the invention, the IL-12 is adsorbed onto a mineral suspension such as alum (e.g., aluminum hydroxide or aluminum phosphate). These vaccine compositions modulate the protective immune response to the antigen; that is, the vaccine composition is capable of eliciting the vaccinated host's complement-fixing antibodies for a protective response to the pathogen. In a particular embodiment of the invention, the antigen is a pneumococcal antigen, particularly a pneumococcal polysaccharide; the pneumococcal antigen is optionally conjugated to a carrier molecule, such as in a pneumococcal glycoconjugate. The particular pneumococcal polysaccharide serotypes exemplified herein are serotypes 1, 4, 5, 6B, 9V, 14, 18C, 19F, and 23F; however, these serotypes are not to be construed to limit the scope of the invention, as other serotypes are also suitable for use herein.

In another embodiment of the invention, the antigen is a meningococcal antigen, particularly a meningococcal polysaccharide; the meningococcal antigen is optionally conjugated to a carrier molecule, such as in a meningococcal glycoconjugate. Type C *Neisseria meningitidis* is exemplified herein; however, this type is not to be construed to limit the scope of the invention, as other types are also suitable for use herein.

IL-12 can be obtained from several suitable sources. It can be produced by recombinant DNA methodology; for example, the gene encoding human IL-12 has been cloned and expressed in host systems, permitting the production of large quantities of pure human IL-12. Also useful in the present invention are biologically active subunits or fragments of IL-12. Commercial sources of recombinant human and murine IL-12 include Genetics Institute, Inc. (Cambridge, Mass.).

The antigen of this invention, e.g., a pneumococcal or meningococcal antigen or a pneumococcal or meningococcal glycoconjugate, can be used to elicit an immune response to an antigen in a mammalian host. For example, the antigen can be a serotype 14 or 6B pneumococcal polysaccharide or a portion thereof which retains the ability to stimulate an immune response. Additional suitable antigens include polysaccharides from other encapsulated bacteria and conjugates thereof, secreted toxins and outer membrane proteins.

The method comprises administering to the mammal, e.g., human or primate, an immunologically effective dose of a vaccine composition comprising a mixture of an antigen, such as a pneumococcal antigen or a pneumococcal conjugate, and an adjuvant amount of IL-12 adsorbed onto a mineral in suspension.

As used herein, an "immunologically effective" dose of the vaccine composition is a dose which is suitable to elicit an immune response. The particular dosage of IL-12 and the antigen will depend upon the age, weight and medical condition of the mammal to be treated, as well as on the method of administration. Suitable doses will be readily determined by the skilled artisan. The vaccine composition can be optionally administered in a pharmaceutically or physiologically acceptable vehicle, such as physiological saline or ethanol polyols such as glycerol or propylene glycol.

The vaccine composition may optionally comprise additional adjuvants such as vegetable oils or emulsions thereof, surface active substances, e.g., hexadecylamin, octadecyl amino acid esters, octadecylamine, lysolecithin, dimethyldioctadecylammonium bromide, N,N-dicoctadecyl-N'-N'bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions; liposaccharides such as MPL® and mineral gels. The antigens of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed. The antigens of the present invention can also be administered in combination with bacterial toxins and their attenuated derivatives. The antigens of the present invention can also be administered in combination with other lymphokines, including, but not limited to, IL-2, IL-3, IL-15, IFN-γ and GM-CSF.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration. The amount of antigen employed in such vaccines will vary depending upon the identity of the antigen. Adjustment and manipulation of established dosage ranges used with traditional carrier antigens for adaptation to the present vaccine is well within the ability of those skilled in the art. The vaccines of the present invention are intended for use in the treatment of both immature and adult warm-blooded animals, and, in particular, humans. Typically, the IL-12 and the antigen will be co-administered; however, in some instances the skilled artisan will appreciate that the IL-12 can be administered close in time cut prior to or after vaccination with the antigen.

The pneumococcal and meningococcal antigens of the present invention can be coupled to a carrier molecule in order to modulate or enhance the immune response. Suitable carrier proteins include bacterial toxins rendered safe by chemical or generic means for administration to mammals and immunologically effective as carriers. Examples include pertussis, diphtheria, and tetanus toxoids and non-toxic mutant proteins (cross-reacting materials (CRM)), such as the non-toxic variant of diphtheria toxoid, $CRM_{197}$. Fragments of the native toxins or toxoids, which contain at least one T-cell epitope, are also useful as carriers for antigens, as are outer membrane protein complexes. Methods for preparing conjugates of pneumococcal antigens and carrier molecules are well known in the art and can be found, for example, in Dick and Burret, *Contrib Microbiol Immunol.* 10:48–114 (Cruse J M, Lewis R E Jr, eds; Basel, Krager (1989)) and U.S. Pat. No. 5,360,897 (Anderson et al.).

The adjuvant action of IL-12 has a number of important implications. The adjuvanticity of IL-12 can increase the concentration of protective functional antibodies produced against the antigen in the vaccinated organism. The use of IL-12 as an adjuvant can enhance the ability of antigens which are weakly antigenic or poorly immunogenic to elicit an immune response. It may also provide for safer vaccination when the antigen is toxic at the concentration normally required for effective immunization. By reducing the amount of antigen, the risk of toxic reaction is reduced.

Typically, vaccination regimens call for the administration of antigen over a period of weeks or months in order to stimulate a "protective" immune response. A protective immune response is an immune response sufficient to protect the immunized organism from productive infection by a particular pathogen or pathogens to which the vaccine is directed.

As shown in the Examples, in an alum-formulated vaccine, comprising IL-12 adsorbed onto $AlPO_4$ and a serotype 14 or serotype 6B pneumococcal polysaccharide conjugated to $CRM_{197}$, which normally induces a response dominated by IgG1, 0.2 µg of IL-12 substantially increased the IgG2a and IgG3 subclasses in both Balb/c and Swiss Webster mice, but had little or no effect on IgG1. Enhancement of IgG2b to Pn14 was seen with Swiss Webster mice; 0.2 µg of IL-12 had the same effect as 25 µg of MPL® on the IgG subclass response to Pn14, suggesting that IL-12 is at least 100-fold more biologically active than MPL® in this regard. As expected from the IgG subclass distribution, especially the enhanced IgG2a response, the opsonophagocytic activity of the antisera for Pn14 pneumococci from mice receiving 0.2 µg IL-12 was higher than that of controls and was equivalent to that of mice immunized with vaccine formulated with a much larger amount of MPL®.

Briefly, IgG2a and IgG2b antibodies are very efficient at activating the complement system, whereas IgG1 antibodies are not. The complement system consists of a series of plasma proteins which come together around IgG2a or IgG2b bound to antigen (e.g., bacteria) to form a large molecular complex. Deposition of this complex on the surface of bacteria results in the killing of the bacteria by perforating the cell membrane (bactericidal activity) or by facilitating the recognition of the bacteria by phagocytic cells (such as polymorphonuclear cells (PMN) used in this study), which take up the bacteria and kill them (opsonophagocytosis).

Increasing the dose of IL-12 profoundly reduced the IgG1 and IgG2b responses. The reduction in these immunoglobulin subclasses was not simply due to a change in the kinetics of the antibody response, as has been observed in the hen egg lysozyme (HEL) system (Buchanan, Van Cleave and Metzger, Abstract #1945; 9th International Congress of Immunology (1995)), as these subclasses were reduced at all time points tested. The effect on IgG1 was expected given that switching of B cells to this subclass requires IL-4, a TH-2 cytokine whose production is inhibited by IL-12. The reduction in IgG2b, however, was not expected since in previous studies increased levels of IgG2b have correlated with the presence of TH-1-like T cells. It is likely that cytokines other than, or in addition to, IFN-γ are involved in regulation of IgG2b. For example, Germann et al. (Eur J. Immunol 25:823–829 (1995)) found that treating mice with anti-IFN-γ inhibited the ability of IL-12 to promote IgG2a responses, but not IgG2b. Other studies have implicated TGF-β as an important factor in the induction of IgG2b (reviewed by J. Stavnezer, J. Immunol. 55:1547–1651 (1995)). Without wishing to be bound by theory, it is possible that high doses of IL-12 may affect TGF-β production or responsiveness to it.

IFN-γ is critical for the induction of IgG2a antibodies to T-dependent protein antigens (Finkelman and Holmes, Annu. Rev. Immunol. 8:303–33 (1990)) and IgG3 responses to T-independent antigens (Snapper et al., J. Exp. Med. 175:1367–1371 (1992)). Increased IFN-γ response was consistently found after a single vaccination with vaccine (PnPs-14-$CRM_{197}$) containing IL-12 and $AlPO_4$ and after boosting. The effect of IL-12 on the TH-2 cytokines IL-5 and IL-10 appears to depend on when the lymphoid cells are harvested after vaccination, and possibly on the particular cytokine. Exogenous IL-12 completely abolished antigen-specific IL-5 and IL-10 production by lymph node cells (LNC) harvested 1 week after primary vaccination. After secondary vaccination, differences were seen between these two cytokines; IL-5 production by either LNC or splenocytes was completely abolished by 1 µg IL-12 in the vaccine, but IL-10 production was largely unaffected after boosting. It is unclear whether these differences are due to setting up the cultures at different times or reflect the expansion of a TH-2-like population upon subsequent revaccination. The latter possibility is consistent with data from Wolf and colleagues (Bliss et al., J. Immunol 156:887–894 (1996)), indicating that IL-4-producing T cells can be recovered from Balb/c mice previously immunized with vaccine containing IL-12 and boosted with soluble antigen. In their studies, IL-4 was detected even if IL-12 was included in the secondary vaccine. The presence of TH-2 cytokines after boosting may explain why, in Balb/c mice, even high levels of IL-12 could not reduce the secondary IgG1 response to below control levels (conjugate vaccine on alum). Unlike the Balb/c mice, high doses of IL-12 severely inhibited the IgG1 response of Swiss Webster mice. Whether this is associated with decreased production of TH-2 cytokines after the second vaccination is unclear.

In the present studies, IL-12 exhibited either only immunomodulatory activity or behaved both as a "classical" adjuvant, and a immunomodulator, depending on the vaccine. In the study with PnPs14-$CRM_{197}$ the IgG response (especially the primary response) to the vaccine was not substantially elevated by the presence of the cytokine but certain subclasses, i.e. IgG2a and IgG3, were elevated whereas the others were unchanged or diminished. Thus, IL-12 is useful for altering the humoral response to an already immunogenic vaccine. It is possible that in these studies the adjuvant activity of IL-12 was masked by the presence of alum, which is an adequate adjuvant on its own for the highly immunogenic PnPs-14 conjugate. The adjuvanticity of IL-12 may be better demonstrated in the absence of alum, by reducing the dose of conjugate or by using a poorly immunogenic conjugate. Thus, further evaluations were carried out using IL-12 in the presence and absence of alum with PnPs6B conjugate vaccines, which are less immunogenic in Swiss Webster mice than PnPs-14 conjugate vaccines.

An additional study was designed to address the issue of IL-12 adjuvant activity for a poorly immunogenic pneumococcal conjugate. The Pn18C conjugate was chosen, as it is poorly immunogenic when formulated with $AlPO_4$, i.e., it induces low IgG Liters and not all mice respond to it. When formulated with MPL or QS-21, higher IgG fibers and a greater frequency of responders can be achieved.

One hundred µg MPL® plus $AlPO_4$ or 20 µg QS-21™ were the best adjuvants in this study for a Pn18C response as they induced the highest frequency of responders to this serotype. Nonetheless, IL-12 had marked effects on the IgG response to the carrier protein, $CRM_{197}$, in mice immunized with this conjugate. Moreover, the effects of the cytokine were modified by the presence of $AlPO_4$ in the vaccine. IL-12 clearly acted as an adjuvant for vaccines formulated without $AlPO_4$, causing a dose-dependent increase in IgG titers after primary and secondary vaccination. IL-12 enhanced the IgG2a response to $CRM_{197}$, which is consistent with its ability to favor the induction of TH-1-like helper cells (IFN-γ producers). However, IL-12 also enhanced the IgG1 response to $CRM_{197}$ after primary and secondary vaccination. IgG1 antibodies are normally associated with TH-2-like helper cells whit. produce IL-4.

Inclusion of 0.1 μg IL-12 into an $AlPO_4$-based Pn18C conjugate vaccine (which on its own induced a 10-fold higher $CRM_{197}$ response) had no effect on IgG1 but substantially increased the IgG2a titer. The IgG2a titer achieved with 0.1 μg IL-12 was at least as high as that obtained with 5 μg IL-12 the absence of $AlPO_4$. It should be noted, however, that the presence of $AlPO_4$ does not preclude the enhancement of IgG1 responses by IL-12. In mice immunized with the Pn14 conjugate on $AlPO_4$, a 0.2 μg dose of IL-12 enhanced the IgG1, IgG2a and IgG2b titers to $CRM_{197}$. The differences in the effect on IgG1 may reflect differences in the immunogenicity of the two conjugates for $CRM_{197}$ IgG responses; the Pn14 conjugate on $AlPO_4$ induced 10-fold lower $CRM_{197}$ IgG titers so that there was room for IL-12 to enhance an IgG1 response, but not when mice were immunized with Pn18C conjugate on $AlPO_4$. The fact that MPL® and QS-21™ markedly increased the IgG1 titers in mice immunized with Pn18C conjugate on $AlPO_4$ indicates that the IgG1 response had not been maximally stimulated. Alternatively, the nature of the saccharides on the conjugates may be a factor. In both experiments, higher doses of IL-12 resulted in a marked diminution of the IgG1, IgG2a and IgG2b tiers to $CRM_{197}$, an effect that was not seen in the absence of $AlPO_4$.

IL-12 probably exerts its adjuvant effect differently than MPL® or QS-21™. IL-12 markedly enhanced the $CRM_{197,9}$, IgG2a titers in mice immunized with Pn18C conjugate but had minimal effects on IgG2b. In contrast, MPL® and QS-21™ enhanced the titers of both IgG subclasses. The dissociation of these two subclasses suggests that IgG2b is induced by cytokines other than, or in addition to, the IFN-γ that drives switching to IgG2a and is known to mediate the immunomodulatory effects of IL-12. One candidate for driving IgG2b production is TGFb. The nature of the antigen cannot be excluded, however, since in mice immunized with Pn14 conjugate, 0.2 μg IL-12 caused IgG2a and IgG2b to be elevated to similar levels which were equivalent to the titers promoted by 25 μg MPL®.

Studies utilizing a bivalent vaccine consisting of a PnPs14-$CRM_{197}$ conjugate mixed with a conjugate of capsular polysaccharide from serotype 6B pneumococci covalently linked to $CRM_{197}$ (PnPs6B-$CRM_{197}$) confirmed and extended the above-described findings. IL-12 not only modified the IgG response to the Pn6B conjugate, but also enhanced the overall IgG titer to the conjugate. Moreover, this work further demonstrates that the adjuvant activity of relatively low doses of IL-12 is enhanced by formulating it with $AlPO_4$. Unlike the above-described studies with PnPs-14-$CRM_{197}$ glycoconjugate, IL-12/$AlPO_4$ enhanced both the IgG1 and IgG2a subclasses to Pn6B, indicating that the apparent lack of enhancement of the Pn14 IgG1 response by IL-12 is probably not a generalizable phenomenon. This work further supports the idea that the mechanisms of adjuvant activity by IL-12 and MPL® are not equivalent. Both adjuvants enhanced the Pn6B IgG1 and IgG2a titers to similar levels, but MPL® was more effective at promoting IgG2b and IgG3 antibodies.

IL-12/$AlPO_4$ did nor act as an adjuvant for the Pn14 IgG response. The reason for this is not clear; however, without wishing to be bound by theory, this most likely reflects the fact that in previous studies mice were immunized with a 1 μg dose of PnPs-14-$CRM_{197}$ glycoconjugate, i.e., 10-fold higher than in the Pn6B studies. The applicability of IL-12 to more complex pneumococcal vaccines was demonstrated using a nonavalent vaccine containing glycoconjugates from serotype 1, 4, 5, 6B, 9V, 14, 18C, 19F and 23F pneumococci. The combination of IL-12 with $AlPO_4$ enhanced the IgG2a antibodies to PnPs4 and PnPs9V, in addition to PnPs6B and PnPs14, and increased the ability of mice to respond to glycoconjugate prepared with serotype 18C pneumococcal saccharide (PnPs-18C-$CRM_{197}$) which is poorly immunogenic in mice.

In further examples, IL-12 was tested with a glycoconjugate vaccine against type C *Neiserria meningitidis* (MenC) and a glycoconjugate vaccine against type B *Hemophilus influenzae* (HbOC). Formulating that vaccine with 50 ng IL-12 and $AlPO_4$ enhanced the IgG2a titers to MenC capsular polysaccharide although not to HbOC.

The data presented herein indicate that $AlPO_4$ can greatly enhance the potency of IL-12 so that substantially lower doses of the cytokine can be used. One possible mechanism is that IL-12 binds to $AlPO_4$, thereby enhancing its persistence in the animal; additional studies indicate that IL-12 rapidly binds to alum (data not shown). Alternatively, the local inflammatory effect of $AlPO_4$ may induce cytokines that potentiate the biological activity of IL-12.

In addition to understanding the physical interaction of IL-12 with $AlPO_4$, several other issues arise from the present work with pneumococcal vaccines formulated with IL-12. Given that $AlPO_4$ enhances the activity of IL-12, it would be useful to know the minimal dose of cytokine needed to adjuvant the IgG response to pneumococcal glycoconjugates, as well as whether IL-5-producing T cells are activated by IL-12-containing glycoconjugate vaccines. These two questions were addressed in the studies in Balb/c mice described in Example 4.

The following Examples are offered for the purpose of illustrating the present invention and are not to be construed to limit the scope of this invention. The teachings of all references cited herein are hereby incorporated herein by reference.

EXAMPLES

Example 1

Effect of IL-12 on the IgG Response of Swiss Webster Mice to Serotype 14 Pneumococcal Capsular Polysaccharide Conjugated to $CRM_{197}$ on Aluminum Phosphate (PnPs-14-$CRM_{197}$/$AlPO_4$)

STUDY DESIGN

Swiss Webster mice (10 per group) were immunized twice (at weeks 0 and 3) with 1 μg PnPs-14-$CRM_{197}$ formulated with 100 μg $AlPO_4$ and either no IL-12, 0.2 μg, 1 μg or 5 μg IL-12. All vaccines included 0.25% normal mouse serum for the purpose of stabilizing the IL-12 when used at low concentrations. PnPs14-$CRM_{197}$ is a conjugate of capsular polysaccharide from serotype 14 pneumococci covalently linked to the generically detoxified diphtheria toxin, $CRM_{197}$, by reductive amination. Another group received 25

µg MPL® (3-O-deacylated monophosphoryl lipid A, RIBI Immunochem Research, Inc., Hamilton Montana) instead of IL-12. The vaccinations were given subcutaneously three weeks apart. Sera were collected at week 3 (primary response) and weeks 5 and 7 (secondary responses 2 and 4 weeks after boosting). The sera were analyzed for IgG antibodies to PnPs-14.

The sera were also analyzed for the ability to promote opsonophagocytic killing of type-14 pneumococci by human polymorphonuclear cells (PMN). Type 14 pneumococci were opsonized with dilutions o: antisera and C8-depleted serum as a source of complement. They were then incubated with human polymorphonuclear cells (PMN), and the percent of bacteria surviving was determined by colony counts.

RESULTS

Table 1 shows that 1 µg and 5 µg IL-12 substantially reduced the anti-PnPs-14 IgG response in mice immunized with conjugate formulated with AlPO$_4$. The lowest dose (0.2 µg) of cytokine had no effect on the total IgG response but caused major chances in the levels of the individual immunoglobulin subclasses. At weeks 5 and 7 (2 and 4 weeks after boosting, respectively), 0.2 µg IL-12 induced substantially higher IgG2a, IgG2b and IgG3 titers but left the IgG1 levels essentially unaltered. The IgG subclass profile induced by 0.2 µg IL-12 was indistinguishable from that obtained with 25 µg MPL®, and sera from mice receiving these adjuvants had higher opsonophagocytic activity than those from mice immunized with a vaccine containing only AlPO (Table 2).

The higher doses of IL-12 markedly reduced the IgG1 antibodies; at 5 µg cytokine, IgG1 titers were an least 10-fold lower than in mice immunized without IL-12. This effect was apparent both during the primary response and after boosting. Increasing the IL-12 dose did not cause further increases in IgG2a, IgG2b and IgG3, and, like IgG1, they also declined, although to varying degrees. IgG2b showed the greatest reduction such that vaccines containing 1 µg or 5 µg IL-12 induced the same IgG2b titer as those without adjuvant. IgG2a and IgG3 were less sensitive to the effects of high IL-12 dose; even with 5 µg IL-12, after the second vaccination these subclasses were higher than in the controls.

These studies showed that IL-12 could modulate the IgG subclass response to a PnPs14-CRM$_{197}$ conjugate vaccine formulated with AlPO$_4$. A 0.2 µg dose of IL-12 increased the IgG2a, IgG2b and IgG3 response to Pn14 without affecting the IgG1 response. Higher doses of IL-12 resulted in a marked reduction in the IgG1 and IgG2b titers. IgG2a and IgG3 titers also appeared to decline at these doses, but they were still higher than in mice immunized in the absence of IL-12. Example 2 demonstrates that the IgG subclass changes were associated with enhanced induction of IFN-γ -producing, CRM$_{197}$-specific T cells and a marked reduction in antigen-specific IL-5 production, suggesting a change In the helper cell phenotype from TH-2-like to TH-1-like.

TABLE 1

Effect of IL-12 on the immunogenicity of PnPs-14-CRM$_{197}$/alum vaccine

| Time | Adjuvant | Dose (µg) | PnPs14 IgG Response | | | | |
|---|---|---|---|---|---|---|---|
| | | | IgG | IgG1 | IgG2a | IgG2b | IgG3 |
| week 3 | None | | 56,035 | 8,394 | 481 | 298 | 1,312 |
| | IL-12 | 5 | 13,137 | 480 | 2,417 | 388 | 2,398 |
| | IL-12 | 1 | 26,131 | 1,521 | 3,249 | 736 | 3,858 |
| | IL-12 | 0.2 | 90,220 | 13,779 | 4,731 | 1,454 | 7,944 |
| | MPL® | 25 | 46,451 | 14,303 | 1,506 | 8,506 | 18,203 |
| week 5 | None | | 531,270 | 189,571 | 5,507 | 14,463 | 18,158 |
| | IL-2 | 5 | 231,015 | 16,900 | 28,719 | 6,002 | 56,982 |
| | IL-12 | 1 | 198,044 | 36,327 | 27,420 | 11,841 | 30,740 |
| | IL-12 | 0.2 | 722,360 | 305,623 | 60,701 | 89,397 | 99,794 |
| | MPL® | 25 | 751,066 | 221,324 | 44,957 | 91,265 | 77,989 |
| week 7 | None | | 694,471 | 244,212 | 1,801 | 6,849 | 9,245 |
| | IL-12 | 5 | 177,438 | 17,232 | 20,276 | 3,494 | 26,859 |
| | IL-12 | 1 | 183,571 | 44,213 | 21,246 | 5,063 | 13,447 |
| | IL-12 | 0.2 | 852,292 | 251,157 | 37,104 | 37,717 | 88,933 |
| | MPL® | 25 | 783,622 | 187,055 | 30,694 | 89,153 | 59,297 |

TABLE 2

Opsonophagocytic activity of sera of mice immunized with PnPs-14-CRM$_{197}$/AlPO$_4$ formulated with IL-12 or MPL®

| Initial | % Bacteria Surviving | | | | | | | | | |
|---|---|---|---|---|---|---|---|---|---|---|
| Serum | Week 5 Sera | | | | | Week 7 Sera | | | | |
| Dilution Tested | No. IL-12 | 0.2 µg IL-12 | 1 µg IL-12 | 5 µg IL-12 | 25 µg MPL® | No. IL-12 | 0.2 µg IL-12 | 1 µg IL-12 | 5 µg IL-12 | 25 µg MPL® |
| 2 | 6 | 10 | 6 | 6 | 9 | 6 | 6 | 7 | 7 | 5 |
| 8 | 12 | 7 | 9 | 9 | 7 | 21 | 4 | 10 | 9 | 6 |
| 16 | 32 | 4 | 24 | 25 | 3 | 47 | 8 | 17 | 26 | 8 |
| 32 | 71 | 12 | 61 | 94 | 23 | 68 | 6 | 85 | 90 | 21 |
| 64 | 64 | 46 | 90 | 89 | 51 | 116 | 34 | 79 | 99 | 76 |

Example 2

Nature of T Helper Cells Induced by Pneumococcal Conjugate Vaccine (PnPs-14-CRM$_{197}$/AlPO$_4$) Formulated With IL-12

STUDY DESIGN

Groups of eight (8) Balb/c mice were immunized subcutaneously at the base of the tail with 1 µg PnPs-14-CRM$_{197}$ conjugate formulated with 100 µg AlPO$_4$ and different doses of IL-12. Normal mouse serum (0.25%) was included as a carrier protein. One week later, draining lymph node cell suspensions were prepared from half the mice in each group and cultured with CRM$_{197}$, lysozyme, ConA or in medium alone for 6 days. Culture supernatants from parallel cultures were harvested at day 3 and day 6 and assayed for IFN-γ, IL-5 and IL-10 by ELISA.

At three weeks, the remaining mice were bled and reimmunized with the same vaccine formulation used in the first immunization. Fourteen days after the second immunization (week 5), the mice were bled once more. Four days later their draining lymph node cells and splenocytes were harvested and cultured or six days with $CRM_{197}$, lysozyme, ConA or in medium alone. Culture supernatants from parallel cultures were harvested at day 3 and day 6 and assayed for IFN-γ, IL-5 and IL-10 by ELISA.

RESULTS

Formulating $PnPs-4-CRM_{197}/AlPO_4$ vaccine with the lower doses of IL-12 (0.2 μg and 1.0 μg) greatly enhanced the IgG2a and IgG3 responses to Pn14 at week 5, but not IgG1 (see Table 3) Several differences were seen between the results obtained with Balb/c mice and Swiss Webster mice in the previous experiment; in this experiment IL-12 did not dramatically increase the IgG2b antibodies to Pn14, nor did the 5 μg IL-12 dose cause the dramatic (>10-fold) reduction in IgG1 titers relative to the control group without cytokine.

One week after immunization, lymph node cells from mice immunized without IL-12 produced IFN-γ, IL-5 and IL-10 when stimulated with $CRM_{197}$ in vitro (Table 4) Adding IL-12 to the vaccine dramatically increased the antigen-specific production of IFN-γ and abolished the ability of the lymdhoid cells to produce IL-5 and IL-10. Maximal IFN-γ production was obtained with the lowest dose of IL-12 (0.2 μg); higher doses, particularly 5 μg, appeared to reduce the levels of this cytokine. This was most clearly seen in cultures simulated with 1 μg/mL $CRM_{197}$. The reduction in IFN-γ with higher doses of IL-12 may not reflect a generalized suppressive phenomenon since IFN-γ production in response to ConA was the same regardless of the dose of IL-12 in the vaccine.

Two weeks after the second immunization, lymph node cells and splenocytes from mice immunized with vaccine containing IL-12 continued to produce elevated levels of IFN-γ in response to stimulation with $CRM_{197}$ compared to mice immunized without IL-12 (Table 5). As observed 7 days after primary vaccination, 0.2 μg to 1.0 μg IL-12 were optimal doses of IL-12 for augmentation of an IFN-γ response. In contrast, however, IL-5 and IL-10 production were differentially affected. The 1.0 and 5.0 μg doses of IL-12 essentially eliminated the IL-5 response but, by comparison, had only a minor effect on IL-10 production. IL-12 (5.0 μg) abolished the ability of splenocytes but not lymph node cells to produce IL-10 (Tables 5 and 6).

TABLE 3

Effect of IL-12 on immune response to an alum-based PnPs14 glycoconjugate vaccine in Balb/c Mice

| Week | IL-12 Dose | IgG | IgG1 | IgG2a | IgG2b | IgG3 |
|---|---|---|---|---|---|---|
| 3 | none | 41,480 | 7,347 | 1,387 | 895 | 2,333 |
|   | 0.2 | 26,253 | 1,521 | 1,118 | 171 | 5,911 |
|   | 1 | 26,124 | 966 | 2,155 | 248 | 5,991 |
|   | 5 | 10,753 | 541 | 671 | 183 | 3,242 |

TABLE 3-continued

Effect of IL-12 on immune response to an alum-based PnPs14 glycoconjugate vaccine in Balb/c Mice

| Week | IL-12 Dose | IgG | IgG1 | IgG2a | IgG2b | IgG3 |
|---|---|---|---|---|---|---|
| 5 | none | 234,220 | 33,284 | 2,896 | 3,105 | 2,487 |
|   | 0.2 | 674,996 | 71,808 | 18,245 | 6,789 | 107,470 |
|   | 1 | 622,714 | 32,022 | 22,749 | 7,853 | 44,350 |
|   | 5 | 224,832 | 19,495 | 10,083 | 1,287 | 25,212 |

TABLE 4

Cytokines produced by lymph node cells taken 7 days after single immunization with PnPs-14 conjugate formulated with AlPO and IL-12

| | | | Day 6 Cultures | | | |
|---|---|---|---|---|---|---|
| Cytokine | Antigen in vitro | ug/ml | No IL-12 | 0.2 μg IL-12 | 1.0 μg IL-12 | 5.0 μg IL-12 |
| IFN-γ (U/mL) | CRM | 30 | 23.2 | 102.7 | 60.5 | 32.2 |
| | CRM | 1 | <0.75 | 65.2 | 28.6 | 8.7 |
| | Lysozyme | 30 | <0.75 | 2.9 | 6.6 | 4.5 |
| | Con A | 1 | 43.8 | 97.1 | 107.1 | 105.4 |
| | Medium | — | <0.75 | 3.6 | 10.6 | 5.2 |
| IL-5 (ng/mL) | CRM | 30 | 7.2 | <0.22 | <0.22 | <0.22 |
| | CRM | 1 | 2.2 | <0.22 | <0.22 | <0.22 |
| | Lysozyme | 30 | <0.22 | <0.22 | <0.22 | <0.22 |
| | Con A | 1 | <0.22 | <0.22 | <0.22 | <0.22 |
| | Medium | — | <0.22 | <0.22 | <0.22 | <0.22 |
| IL-10 (ng/mL) | CRM | 30 | 10.4 | 0.8 | 0.21 | 0.21 |
| | CRM | 1 | 2.6 | 0.21 | 0.21 | 0.21 |
| | Lysozyme | 30 | <0.14 | 0.21 | 0.21 | 0.21 |
| | Con A | 1 | <0.14 | 0.21 | 0.21 | 0.21 |
| | Medium | — | <0.14 | 0.21 | 0.21 | 0.21 |

TABLE 5

Cytokine production by splenocytes two weeks after secondary vaccination with PnPs-14 conjugate formulated with AlPO and IL-12

| | | | Day 6 Cultures | | | |
|---|---|---|---|---|---|---|
| Cytokine | Antigen in vitro | ug/ml | No IL-12 | 0.2 μg IL-12 | 1.0 μg IL-12 | 5.0 μg IL-12 |
| IFN-γ (U/mL) | CRM | 30 | 7.0 | 98.4 | 83.2 | 50.9 |
| | CRM | 1 | 1.0 | 89.2 | 76.8 | 16.4 |
| | Lysozyme | 30 | <0.4 | <0.4 | <0.3 | <0.3 |
| | Con A | 1 | 42.7 | 48.7 | 50.6 | 49.5 |
| IL-5 (ng/mL) | CRM | 30 | 13.2 | 3.1 | 0.6 | <0.2 |
| | CRM | 1 | 4.5 | 4.4 | 0.8 | <0.2 |
| | Lysozyme | 30 | <0.3 | <0.3 | 0.2 | <0.2 |
| | Con A | 1 | <0.3 | <0.3 | <0.2 | <0.2 |
| IL-10 (ng/mL) | CRM | 30 | 8.6 | 4 | 7.1 | 0.6 |
| | CRM | 1 | 1.1 | 2.5 | 1.7 | <0.2 |
| | Lysozyme | 30 | <0.2 | <0.2 | 0.3 | <0.2 |
| | Con A | 1 | 0.5 | 0.4 | <0.3 | <0.2 |

TABLE 6

Cytokine production by lymph node cells two weeks after secondary vaccination with PnPs-14 conjugate formulated with AlPO and IL-12

| Cytokine | Antigen in vitro | ug/ml | Day 6 Cultures | | | |
|---|---|---|---|---|---|---|
| | | | No IL-12 | 0.2 μg IL-12 | 1.0 μg IL-12 | 5.0 μg IL-12 |
| IFN-γ (U/mL) | CRM | 30 | 9.8 | 86.9 | 58.7 | 62.0 |
| | CRM | 1 | 0.6 | 78.6 | 62.9 | 36.8 |
| | Lysozyme | 30 | <0.4 | <0.4 | <0.3 | <0.3 |
| | Con A | 1 | 17.7 | 57.6 | 45.7 | 69.0 |
| IL-5 (ng/mL) | CRM | 30 | 12.5 | 1.4 | <0.2 | 0.5 |
| | CRM | 1 | 4.8 | 2.2 | <0.2 | <0.2 |
| | Lysozyme | 30 | <0.3 | <0.3 | <0.2 | <0.2 |
| | Con A | 1 | 1.1 | <0.3 | <0.2 | <0.2 |
| IL-10 (ng/mL) | CRM | 30 | 11.3 | 9.9 | 7.2 | 3.6 |
| | CRM | 1 | 4.4 | 5.5 | 3.3 | 1 |
| | Lysozyme | 30 | <0.2 | <0.2 | <0.2 | <0.2 |
| | Con A | 1 | <0.2 | <0.2 | <0.2 | <0.2 |

Example 3

IL-12 Adjuvant Activity With Poorly Immunogenic Pneumococcal Conjugate

Study Design

Swiss-Webster mice (10 per group) were immunized with 1 μg Pn18C conjugate formulated with or without 100 μg AlPO$_4$. The vaccines were supplemented with either IL-12 (0.2, 1 or 5 μg), 100 μg MPL® or 20 μg QS-21™. Normal mouse serum 0.5% final) was used to stabilize the diluted IL-12 and was added to all vaccines, regardless of composition. Three weeks later, the mice were bled and boosted with the same vaccine formulation used at the primary immunization. Bleeds were also taken at weeks 5 and 7 of the study (2 and 4 weeks after boosting, respectively). Pooled sera were tested at week 5 for Pn18C and CRM$_{197}$ total IgG and IgG subclasses. To determine the frequency of responders to Pn18C, the sera for individual mice were diluted 1/500 and tested by ELISA for IgG antibodies to Pn18C. Results are reported as optical density.

Results

The Pn18C IgG responses are presented in Table 7. The addition if IL-12 to alum-formulated conjugate vaccine had no consistent effect on the IgG response to Pn18C. A dose of 5 μg of IL-12 caused a 3-fold rise in the IgG titer of pooled week 5 sera, whereas vaccine formulated with 1 μg of IL-12 appeared to induce no Pn18C response. The lowest dose of IL-12 (0.1 μg) induced the same response as the AlPO$_4$-formulated vaccine not containing IL-12. The vaccine formulated with MPL®/AlPO$_4$ induced the highest frequency of responses; 7/10 mice gave OD>0.2, in contrast to QS-21™/AlPO$_4$ and AlPO$_4$ alone, each of which induced 4/10 responders. Mice immunized with vaccine containing IL-12 plus AlPO$_4$ induced 2/10, 0/10 and 1/10 responders at IL-12 doses of 0.1 μg, 1.0 μg, and 5 μg, respectively.

In this experiment MPL® and QS-21™ caused at most a 3- to 4-fold increase in the Pn18C IgG response. In the absence of AlPO$_4$, IL-12 did not have a profound adjuvant effect on the Pn18C IgG response. The vaccine containing a 1 μg dose of IL-12 induced the same Pn18C response as vaccine without IL-12. Vaccines containing the lower and higher doses of IL-12 appeared to induce lower responses than the control vaccine. Neither MPL® nor QS-21™ appeared to enhance the Pn18C IgG response. Among the vaccines formulated without AlPO$_4$, QS-21™ induced the highest frequency of responders (7/10 with OD>0.2), whereas all other formulations induced 4/10 responders, at most.

To confirm that the IL-12 in the vaccine was indeed active, the CRM$_{197}$ IgG response in these mice was evaluated. Tables 8 and 9 show that after primary (week 3) and secondary (week 5) vaccination, IL-12 causes a dose-dependent increase in CRM$_{197}$ IgG response in mice immunized with vaccine formulated without AlPO$_4$. Moreover, there was an IL-12 dose-dependent increase in both IgG1 and IgG2a titers at weeks 3 and 5, as well as an increase in IgG2b at week 5. The IgG1 and IgG2a titers at week 5 were similar to those induced by vaccine formulated with 100 μg MPL®. In contrast, the IgG2b titers promoted by IL-12 were 20-fold lower than those induced by MPL® . These data suggest that IgG2a and IgG2b are controlled by different mechanisms, IgG2a being dependent on a mechanism activated by IL-12 and IgG2b being controlled by an IL-12-independent mechanism. These data clearly indicate that IL-12 can act as adjuvant for IgG responses to a protein antigen. Moreover the increase in both IgG1 and IgG2a titers suggest that, within this model at least, IL-12 enhances priming of both TH-1-like and TH-2-like helper cells by PnOs18C-CRM$_{197}$ conjugate in the absence of AlPO$_4$.

When added to the Pn18C conjugate vaccine formulated with AlPO$_4$, the 0.1 μg dose of IL-12 caused little if any increase in the week 3 total IgG response to CRM$_{197}$ but a 3-fold increase at week 5. However, this dose of IL-12 increased the IgG2a titer at week 5, promoting titers similar to that induced by vaccine containing MPL or QS-21. IL-12 did not markedly increase the IgG2b titers. As seen in previous experiments, higher doses of IL-12 resulted in a sharp decline in IgG titers with all subclasses being affected.

TABLE 7

Effect of IL-12 on IgG response to PnOs18C conjugate

| | IgG titer | | IgG subclasses at Week 5 | | | |
|---|---|---|---|---|---|---|
| Adjuvant (μg/dose) | wk 3 | wk 5 | IqG1 | IgG2a | IgG2b | IgG3 |
| AlPO | <100 | 4,608 | 4,591 | 116 | <100 | <100 |
| 0.1 μg IL-12 + AlPO$_4$ | <100 | 3,681 | 1,472 | 265 | 259 | 450 |
| 1.0 μg IL-12 + AlPO$_4$ | <100 | 138 | <100 | <100 | <100 | <100 |
| 5.0 μg IL-12 + AlPO$_4$ | 260 | 13,545 | 7,820 | 1,426 | <100 | 1,481 |
| 100 μg MPL/AlPO$_4$ | 233 | 9,027 | 1,522 | 935 | 877 | <100 |
| QS-21 + AlPO$_4$ | <100 | 7,989 | 879 | 1,395 | 1,062 | 1,004 |
| none | 1.07 | 10,768 | 5,238 | 345 | <100 | 144 |
| 0.1 μg IL-12 | <100 | 1,808 | 336 | 105 | <100 | <100 |
| 1.0 μg IL-12 | <100 | 22,257 | 12,443 | 671 | 172 | 773 |
| 5.0 μg IL-12 | <100 | 460 | 203 | <100 | <100 | 480 |
| 100 μg MPL | 112 | 1,729 | 524 | 363 | 189 | 126 |
| QS-21 | <100 | 3,573 | 2,483 | 101 | <100 | 113 |

TABLE 8

Effect of IL-12 on CRM$_{10}$ IgG response three weeks after vaccination with PnOs18C conjugate

| Adjuvant (μg/dose) | IgG | IgG1 | IgG2a |
|---|---|---|---|
| AlPO$_1$ | 70,964 | 8,706 | 3,516 |
| 0.1 μg IL-12 + AlPO$_4$ | 103,589 | 4,754 | 13,025 |

TABLE 8-continued

Effect of IL-12 on CRM$_{10}$ IgG response three weeks after vaccination with PnOs18C conjugate

| Adjuvant (μg/dose) | IgG | IgG1 | IgG2a |
| --- | --- | --- | --- |
| 1.0 μg IL-12 + AlPO$_4$ | 26,927 | 506 | 2,926 |
| 5.0 μg IL-12 + AlPO$_4$ | 19,579 | 241 | 2,665 |
| 100 μg MPL ®/AlPO$_4$ | 651,315 | 92,245 | 79,508 |
| QS-21 ™/ALPO$_4$ | 572,255 | 116,583 | 38,419 |
| None | 7,630 | 452 | 1,023 |
| 0.1 μg IL-12 | 32,403 | 3,475 | 3,713 |
| 1.0 μg IL-12 | 60,987 | 4,615 | 5,951 |
| 5.0 μg IL-12 | 128,697 | 10,498 | 10,686 |
| 100 μg MPL ®/TEM | 462,289 | 40,010 | 24,979 |
| QS-21 ™ | 556,440 | 111,533 | 53,799 |

TABLE 9

Effect of IL-12 on CRM197 IgG response five weeks after vaccination with PnOs18C conjugate (two weeks after boosting)

| Adjuvant (μg/dose) | TgG | IgG1 | IgG2a | IgG2b |
| --- | --- | --- | --- | --- |
| AlPO$_4$ | 634,631 | 102,974 | 45,955 | 8,812 |
| 0.1 μl IL-12 + AlPO$_4$ | 2,225,000 | 88,204 | 317,083 | 16,869 |
| 1.0 μg IL-12 + AlPO$_4$ | 105,765 | 8,018 | 12,598 | 1,096 |
| 5.0 μg IL-12 + AlPO$_4$ | 71,618 | 1,582 | 13,806 | 744 |
| 100 μg MPL ®/AlPO$_4$ | 4,384,000 | 637,655 | 371,652 | 111,646 |
| QS-21 ™/ALPO$_4$ | >5,000,000 | >1,000,000 | 873,674 | 144,132 |
| None | 62,341 | 12,783 | 3,655 | 1,679 |
| 0.1 μg IL-12 | 296,791 | 52,288 | 23,741 | 7,069 |
| 1.0 μg IL-12 | 1,026,060 | 101,381 | 96,024 | 11,862 |
| 5.0 μg IL-12 | 1,367,771 | 74,494 | 108,815 | 14,258 |
| 100 μg MPL ®/TEM | 4,173,765 | 264,691 | 266,160 | 303,662 |
| QS-21 ™ | >5,000,000 | 1,303,508 | 445,712 | 131,991 |

Example 4

Effect of IL-12 on the IgG Response of Swiss Webster Mice to Bivalent Vaccine Containing PnPs53-CRM$_{197}$ and PnPs-14-CRM$_{197}$

STUDY DESIGN

Swiss Webster mice were immunized subcutaneously at weeks 0 and 3 with a vaccine comprising 0.1 μg per dose of PnPs6B-CRM$_{197}$ glycoconjugate (a conjugate of capsular polysaccharide from serotype 6B pneumococci covalently linked to CRM$_{197}$) plus 0.1 μg per dose of PnPs14-CRM$_{197}$ glycoconjugate. The vaccines were administered with 0, 8, 40, or 200 ng IL-12, either alone or in combination with 100 μg alum (AlPO$_4$). Normal mouse serum (0.25%) was included as a carrier protein to stabilize the IL-12 at low concentrations. A control group of mice was immunized with the vaccine formulated with 100 μg monophosphoryl lipid A (MPL®). The mice were bled at week 3 (primary response) and week 5 (secondary response). Sera were tested for IgG antibodies to Pn6B and Pn14 capsular polysaccharide by ELISA.

RESULTS

Response to PnPs6B Conjugate

Table 10 illustrates the pooled serum IgG response to the Pn6B component of the bivalent vaccine. Little or no response to Pn53 was detected at week 3 if the vaccine contained no adjuvant or was formulated with only AlPO$_4$. The highest titers after a single vaccination appeared to be induced by vaccine containing either MPL® or 8–40 ng of IL-12 co-formulated with alum These titers however were low, i.e., less than 3,000. The week 5 responses show that after boosting, vaccines formulated with 40 ng IL-12 plus AlPO$_4$ or with MPL® induced the highest IgG titers to Pn6B. In the absence of alum, IL-12 in the 8 to 200 ng dose range did not enhance the IgG titers to Pn6B.

The IgG subclass response to Pn6B at week 5 is shown in Table 10. The titers of individual IgG subclasses were similar in mice immunized with vaccine containing no adjuvant or vaccine formulated with AlPO$_4$ (no IL-12). Moreover, formulating the vaccines with 8–200 ng of IL-12 in the absence AlPO$_4$ did not alter the IgG subclass response. In contrast, these doses of IL-12 when combined with AlPO$_4$ resulted in substantially increased IgG1 and IgG2a titers to Pn6B. These titers were similar to those obtained with vaccine formulated with MPL®. IL-12 also increased the IgG2b and IgG3 titers induced by vaccine formulated with AlPO$_4$; however, these titers appeared to be substantially lower than those induced by vaccine formulated with MPL®.

To determine if the increases obtained with a combination of IL-12 and AlPO$_4$ were statistically significant, the Pn6B IgG titers of individual mice in selected groups were determined. The geometric mean titers (GMT) are presented Table 11. The data indicate that groups immunized with vaccines formulated without adjuvant or with AlPO$_4$ alone had similar GMT against Pn6B. Formulating the vaccine with AlPO plus 40 ng IL-12 resulted in a 29-fold increase in titer over that induced by vaccine containing no adjuvant. When all the data were tested by ANOVA (analysis of variance by JMP software; SAS Institute, Cary, N.C.), no statistically significant differences were found. Upon comparison of subsets of data, ANOVA indicated a statistically significant difference when comparing the week 5 responses induced by vaccine containing no adjuvant and vaccines formulated with AlPO$_4$ and various doses of IL-12. Of these, The vaccine formulated with AlPO$_4$ plus 40 ng IL-12 induced a significantly higher Pn6B titer than vaccine formulated without adjuvant. As a further indication of the heightened immunogenicity of that formulation, 7 of the 10 mice in that group had Pn6B titers greater than or equal to 50,000 compared to only 1 and 2 mice each in the groups vaccinated with conjugate formulated without adjuvant or with AlPO$_4$ alone.

TABLE 10

Effect of IL-12 on the IgG response to PnPs6B in mice immunized with a bivalent PnPs6B/14 pneumococcal glycoconjugate vaccine

| | | Pn6B IgG Titer* | | Pn6B IgG Subclass Response at Week 5* | | | |
| --- | --- | --- | --- | --- | --- | --- | --- |
| Group | Adjuvant | Week 3 | Week 5 | IgG1 | IgG2a | IgG2b | IgG3 |
| P344 | 200 ng IL-12 + | 630 | 161,867 | 19,474 | 22,664 | 2,954 | 7,333 |
| P345 | 40 ng IL-12 + | 2,609 | 429,006 | 61,364 | 24,172 | 4,117 | 9,830 |
| P346 | 8 ng IL-12 + AlPO$_4$ | 1,977 | 284,206 | 46,734 | 32,859 | 3,195 | 8,764 |

TABLE 10-continued

Effect of IL-12 on the IgG response to PnPs6B in mice immunized with a bivalent PnPs6B/14 pneumococcal glycoconjugate vaccine

| Group | Adjuvant | Pn6B IgG Titer* | | Pn6B IgG Subclass Response at Week 5* | | | |
|---|---|---|---|---|---|---|---|
| | | Week 3 | Week 5 | IgG1 | IgG2a | IgG2b | IgG3 |
| P347 | AlPO$_4$ (no IL-12) | 279 | 120,999 | 8,767 | 2,199 | 688 | 301 |
| P348 | 200 ng IL-12 | <100 | 22,401 | 6,816 | 3,147 | 501 | 1,104 |
| P349 | 40 ng IL-12 | 164 | 23,343 | 5,056 | 2,532 | 879 | 292 |
| P350 | 8 ng IL-12 | 642 | 81,748 | 17,702 | 3,573 | 5,151 | 1,786 |
| P351 | None | <100 | 20,153 | 3,061 | 1,506 | 364 | 1,220 |
| P352 | 100 µg MPL® | 2,872 | 840,513 | 84,660 | 30,813 | 43,505 | 25,749 |

*Pooled serum titers

TABLE 11

Pn6B IgG titers of individual mice

| | Group | | | | | | |
|---|---|---|---|---|---|---|---|
| Mouse # | P344 AlPO$_4$ + 200 ng IL-12 | P345 AlPO$_4$ + 40 ng IL-12 | P346 AlPO$_4$ + 8 ng IL-12 | P347 AlPO$_4$ (no IL-12) | P350 8 ng IL-12 | P351 No Adjuvant | P352 100 µg MPL® |
| 1 | 1,957 | 596,886 | 13,457 | 306,012 | 833,148 | 3,544 | 7,556 |
| 2 | 2,498 | 1,205 | 1,000,000 | 3,653 | 9,431 | 326 | 1,359,470 |
| 3 | 100 | 9,453 | 1,422 | 8,708 | 3,163 | 1,136 | 81 |
| 4 | 11,830 | 70,278 | 168,481 | 41,395 | 109,399 | 24,140 | 583,097 |
| 5 | 1,823 | 157,427 | 16,454 | 677,407 | 252 | 50,785 | 86,656 |
| 6 | 6,114 | 90,843 | 989 | 9,089 | 150,245 | 228 | 284 |
| 7 | 279 | 49,182 | 372,709 | 17,164 | 112 | 1,351 | 1,000,000 |
| 8 | 756,503 | 408,348 | 425 | 7,329 | 393 | 36,805 | 473,652 |
| 9 | 1,000,000 | 1,000,000 | 667,988 | 100 | 13,622 | 22,817 | 927,213 |
| 10 | 177 | 1,052,210 | 6,206 | 245 | 182,629 | 851 | — |
| GMT | 4,347 | 103,743 | 22,580 | 9,735 | 10,120 | 3,589 | 55,799 |
| Mice with titer ≥50,000 | 2 | 7 | 4 | 2 | 4 | 1 | 6 |

Statistical Comparisons (ANOVA: α = 0.05)
AlPO$_4$ + 40 ng IL-12 vs. no adjuvant: significant

Response to PnPs14 Conjugate

The IgG response to the PnPs14 component of the vaccine is shown in Table 12. The data indicate that IL-12 in the 8–40 ng dose range, either alone or when formulated with AlPO$_4$, did not enhance the response to PnPs14 after primary or secondary vaccination. Moreover, subclass analysis indicated that IL-12 did not enhance the IgG2a titers when formulated with IL-12. In this study, MPL® did not have the profound adjuvant effect on the PnPs14 response there was observed in previous studies, at least when assaying pooled sera. To get an idea or the degree of variation or the response of each group, individual sera were assayed Pn14 IgG antibodies at a 1/300 dilution The results presented in Table 13 suggest that there was large range of responses in each group, i.e., the Coefficient of Variation (CV) ranged from 0.229 to 0.587, with the exception of the group immunized with vaccine containing MPL® where the CV was 0.051. Thus, it appeared that MPL®, but not IL-12, may have acted as an adjuvant or the Pn14 IgG response and reduced the mouse-to-mouse variation.

TABLE 12

Effect of IL-12 on the IgG subclass response to Pn14 in mice immunized with a bivalent PnPs6B/14 pneumococcal glycoconjugate vaccine

| | PnPs14 Ig* Titer* | | PnPs14 IgG Subclass at Week 5* | | | |
|---|---|---|---|---|---|---|
| Adjuvant | Week 3 | Week 5 | IgG1 | IgG2a | IgG2b | IgG3 |
| 200 ng IL-12 + AlPO$_4$ | 2,170 | 58,657 | 6,880 | 8,996 | 1,945 | 5,995 |
| 40 ng IL-12 + AlPO$_4$ | 1,641 | 53,557 | 8,646 | 3,003 | 3,684 | 2,745 |
| 8 ng IL-12 + AlPO$_4$ | 2,181 | 85,173 | 10,094 | 11,346 | 5,328 | 2,560 |
| AlPO$_4$ (no IL-12) | 2,102 | 201,082 | 54,989 | 4,030 | 6,402 | 3,745 |
| 200 ng IL-12 | 849 | 18,293 | 5,769 | 1,582 | 536 | 799 |
| 40 ng IL-12 | 1,544 | 11,442 | 4,350 | 714 | 514 | 455 |

TABLE 12-continued

Effect of IL-12 on the IgG subclass response to
Pn14 in mice immunized with a bivalent PnPs6B/14
pneumococcal glycoconjugate vaccine

| Adjuvant | PnPs14 Ig* Titer* | | PnPs14 IgG Subclass at Week 5* | | | |
|---|---|---|---|---|---|---|
| | Week 3 | Week 5 | IgG1 | IgG2a | IgG2b | IgG3 |
| 8 ng IL-12 | 113 | 12,169 | 5,286 | 354 | 245 | 330 |
| None | 509 | 22,601 | 6,080 | 808 | 618 | 694 |
| 100 µg MPL ® | 18,616 | 77,106 | 15,745 | 4,275 | 10,205 | 3,916 |

*Pooled serum titers

TABLE 13

Response of individual mice to Pn14 component
of Pn6B/Pn14 bivalent pneumococcal conjugate vaccine*

| Adjuvant | O.D. Range | O.D. Mean | Standard Deviation | Coefficient or Variation |
|---|---|---|---|---|
| AlPO$_4$ + 200 ng IL-12 | 0.034–0.990 | 0.788 | 0.318 | 0.404 |
| AlPO$_4$ + 40 ng IL-12 | 0.457–0.948 | 0.771 | 0.176 | 0.229 |
| AlPO$_4$ + 8 ng IL-12 | 0.023–0.923 | 0.707 | 0.2811 | 0.397 |
| AlPO$_4$ (no IL-12) | 0.328–0.974 | 0.770 | 0.220 | 0.285 |
| 8 ng IL-12 (no alum) | 0.009–0.812 | 0.505 | 0.292 | 0.587 |
| No adjuvant | 0.030–0.876 | 0.614 | 0.343 | 0.558 |
| 100 µg MPL ® | 0.791–0.918 | 0.863 | 0.044 | 0.051 |

*Individual sera tested by ELISA at 1/300 dilution for IgG antibodies to Pn14.

Example 5

Comparison of the Effect of IL-12 in the Presence or Absence of Alum on the Murine Immune Response to Monovalent PnPs14-CRM$_{197}$ Conjugate Vaccine

STUDY DESIGN

BALB/c mice (8 per group) were immunized subcutaneously at week 0 with 1 µg PnPs14-CRM$_{197}$ conjugate formulated with or without 100 µg AlPO$_4$ and either no IL-12 or with 8, 40, 200, 1,000 or 5,000 ng IL-12. Normal mouse serum (0.25%) was included as a carrier protein to stabilize IL-12 at low concentrations. At week 1, lymph node cell suspensions were prepared from half the mice in each group and evaluated for antigen-specific cytokine production in vitro. Their spleens were also harvested and weighed. At week 3 the remaining mice were bled and re-immunized with the same vaccine formulation used in the initial vaccination. At week 5 the twice-immunized mice were bled, their spleens weighed and their splenocytes evaluated for cytokine production. PnPs14 and CRM$_{197}$ IgG and IgG subclass titers were determined on pooled sera. When the assays were performed using sera from individual mice, the results are expressed as geometric mean titers (GMT).

RESULTS
Effect of IL-12 on Spleen Weight One Week After Immunization

One week after the first immunization, mice receiving 5,000 ng IL-12, but not lower doses of IL-12, in the absence of AlPO$_4$, had significantly higher spleen weights than those receiving vaccine containing neither alum nor IL-12 (Table 14). Vaccines containing AlPO$_4$ induced higher spleen weights when formulated with 40 to 5000 ng IL-12. Pairwise comparisons indicated that vaccines formulated with 200 or 1000 ng IL-12 plus AlPO$_4$ induced higher spleen weights than those formulated with the same dose of IL-12 in the absence of AlPO$_4$. Overall, the data indicate that formulating IL-12 with AlPO$_4$ greatly enhanced a biological activity of the cytokine, i.e., its ability to cause increased spleen weight one week after vaccination.

Effect of IL-12 on the IgG Response to PnPs14

Initially, pooled sera were assayed for IgG antibodies to PnPs14 (Table 15). The clearest indication of an adjuvant effect was noted after primary immunization with vaccine containing AlPO$_4$ and 8 to 40 ng IL-12. This combination resulted in a 17- to 21-fold increase in the IgG titer relative to mice immunized with vaccine formulated with neither AlPO$_4$ nor IL-12. The combination of AlPO$_4$ and IL-12 resulted in higher responses than when used individually; on their own AlPO$_4$ and the 40 ng dose of IL-12 caused 4-fold and 5-fold increase in week 3 IgG titers, respectively. Analysis of individual sera from mice immunized with AlPO$_4$-containing vaccines (Table 16) showed that 8 ng IL-12 induced 5-fold higher PnPs14 IgG titers after primary vaccination than vaccine adjuvanted with only AlPO$_4$. The difference in titers was statistically significant. Higher doses of IL-12 did not enhance the response. The 1,000 to 5,000 ng doses of IL-12 caused a marked decline in PnPs14 IgG titers. After the second immunization only the 40 ng dose of IL-12 caused a significant rise (3-fold) in the PnPs14 titer induced by the AlPO$_4$-based vaccine.

The pooled serum data suggest that the combination of AlPO$_4$ and 8–40 ng IL-12 enhanced the IgG1 titers after primary immunization. After two vaccinations, IL-12 did not enhance the IgG1 titers to PnPs14 in mice immunized with conjugate in the absence of AlPO$_4$ as indicated by analysis of pooled (Table 15) and individual sera (Table 17) Moreover, among mice immunized with vaccine containing AlPO$_4$, the addition of 8 to 200 ng IL-12 did not result in higher IgG1 titers after 2 vaccinations (Table 17).

The most profound of IL-12 was to substantially increase the PnPs14 IgG2a response at week 5. This was seen both when the vaccine contained AlPO$_4$ or was formulated without AlPO$_4$ (Table 18). In the absence of AlPO$_4$, statistically significant increases (14- to 42-fold) in IgG2a GMT were obtained with 8 to 1,000 ng IL-12. Similarly, 8–1,000 ng IL-12 enhanced the ability of AlPO$_4$-containing vaccines to induce IgG2a antibodies, although in this study only the titers induced by the 8 and 40 ng doses of IL-12 were statistically higher. Overall, the highest IgG2a titers were induced by conjugate formulated with AlPO$_4$ and 40 ng IL-12. This was significantly different from the IgG2a titers induced by 40 ng IL-12 in the absence of AlPO$_4$, again indicating that the adjuvant activity of IL-12 was enhanced by alum.

IgG2b and IgG3 titers were assayed on pooled sera only (Table 15). Doses of IL-12 in the range of 8 to 1,000 ng when co-formulated with AlPO$_4$, but not in its absence, promoted substantial increases in IgG3 titers after primary and secondary immunization. No consistent effect of IL-12 on the IgG2b titers was noted.

Effect of IL-12 on the IgG Response to CRM$_{197}$

The IgG response to CRM$_{197}$ was also evaluated to see if there were differences between the effect of IL-12 on the protein carrier versus the polysaccharide portion of the conjugate (Table 19). In the absence of AlPO$_4$, 40 ng IL-12 appeared to modestly increase the IgG titers to $CRM_{197}$ after two vaccinations. However, the highest IgG titers to $CRM_{197}$ were obtained when the vaccine was formulated with both $AlPO_4$ and 8–40 ng IL-12. The heightened adjuvant activity of IL-12 co-formulated with $AlPO_4$ is indicated by the finding that, on their own, 40 ng IL-12 and $AlPO_4$ resulted in 6-fold and 17-fold increases in IgG titer at week 5, but when combined together the increase was 147-fold. IL-12 enhanced the IgG1 response to $CRM_{197}$ regardless of whether the vaccine was formulated with or without $AlPO_4$ (Tables 19 and 20). IL-12 substantially increased the week 5 IgG2a titers to $CRM_{197}$ after immunization with vaccines containing $AlPO_4$ (Table 19). Again the optimal dose of IL-12 appeared to be 40 ng. The cytokine appeared to increase the IgG2b titers induced by vaccine containing $AlPO_4$.

Effect of IL-12 on Cytokine Profile of $CRM_{197}$-specific T Cells

Cytokine production by spleen cells taken two weeks after secondary vaccination week (5) revealed effects of IL-12 on the priming of both IFN-γ and IL-5 producing cells. Splenocytes from mice immunized in the absence of $AlPO_4$ and IL-12 produced detectable levels of IL-5, but not IFN-γ, when stimulated with $CRM_{197}$ in vitro (Table 21). Formulating the vaccine with IL-12 appeared to enhance the induction IL-5 producing cells with peak activity occurring with 40 ng of the cytokine. Higher doses of IL-12 resulted in decreased production of IL-5, with virtually no cytokine being produced by mice immunized with conjugate vaccine containing 1,000 to 5,000 ng IL-12. Convincing IFN-γ production was detected only from the splenocytes of mice immunized with vaccines formulated with 5,000 ng IL-12. When the vaccine was formulated with $AlPO_4$, the addition of 8 ng IL-12 resulted in priming of cells that produced copious amounts of IFN-γ, whereas in the absence of the cytokine only antigen-specific IL-5 production was detected. It appears that priming for maximal IFN-γ production occurs with 40 to 1,000 ng IL-12. Addition of 5,000 ng IL-12 abolished the ability of the vaccine to prime for IL-5-producing cells.

TABLE 14

Spleen weights of Balb/c mice one week after subcutaneous immunization with 1 μg PnPs14-CRM - conjugate formulated with cr without 110 μg AlPO and the indicated doses of IL-12

| Adjuvant Formulation | | | Spleen weight (grams) | |
|---|---|---|---|---|
| Group Code | IL-12 (ng) | AlPO | AVERAGE | Standard Deviation |
| P641 | 0 | — | 0.179 | 0.0225 |
| P642 | 2 | — | 0.148 | 0.0112 |
| P643 | 40 | — | 0.162 | 0.0202 |
| P644 | 200 | — | 0.175 | 0.0431 |
| P645 | 1,000 | — | 0.196 | 0.0068 |
| P646 | 5,000 | — | 0.257 | 0.0247 |
| P647 | 0 | — | 0.151 | 0.0158 |
| P648 | 0.151 | 0.0332 | | |
| P649 | 40 | — | 0.217 | 0.0596 |
| P650 | 200 | — | 0.290 | 0.0226 |
| P651 | 1,000 | — | 0.277 | 0.0919 |
| P652 | 5,000 | — | 0.305 | 0.0545 |

Statistical Comparisons (ANOVA; α=0.05)

P642, P643, P644, P645 vs P641: not significant
P646 vs P641: significant
P648 vs P647: not significant
P649, P650, P651, P652 vs P647: significant
P641 vs P647: not significant
P644 vs P650: significant
P642 vs P648: not significant
P645 vs P651: significant
P643 vs P649: not significant
P646 vs P652: not significant

TABLE 15

Anti-PnPs14 IgG response in Balb/c mice immunized with PnPs14-$CRM_{197}$ conjugate formulated with IL-12 and $AlPO_4$

| Adjuvant Formulation | | PnPs14 IgG Titers of Pooled Sera | | | | | | | | | |
|---|---|---|---|---|---|---|---|---|---|---|---|
| | | IgG | | IgG1 | | IgG2a | | IgG2b | | IgG3 | |
| IL-12 (ng) | $AlPO_4$ | Week 3 | Week 5 | Week 3 | Week 5 | Week 3 | Week 5 | Week 3 | Week 5 | Week 3 | Week 5 |
| 0 | − | 1,691 | 24,498 | 479 | 9,967 | 139 | 492 | <100 | <100 | 295 | 1,516 |
| 8 | − | 4,679 | 32,966 | 841 | 9,860 | 377 | 1,902 | 108 | 609 | 390 | 1,354 |
| 40 | − | 6,484 | 50,096 | 1,235 | 17,631 | 207 | 1,209 | 58 | 714 | 1,633 | 4,017 |
| 200 | − | 5,330 | 51,240 | 385 | 7,568 | 715 | 3,748 | 290 | 1,397 | 1,091 | 4,519 |
| 1,000 | − | 6,347 | 69,673 | 1,286 | 12,814 | 859 | 6,532 | 124 | <100 | 782 | 6,208 |
| 5,000 | − | 1,131 | 19,621 | 229 | 3,598 | 126 | 1,392 | <100 | <100 | 635 | 3,616 |
| 0 | + | 7,825 | 103,092 | 1,714 | 38,147 | 195 | 1,535 | 617 | 3,973 | 447 | 2,963 |
| 8 | + | 29,506 | 195,069 | 7,444 | 58,046 | 1,207 | 6,697 | 693 | 4,843 | 5,669 | 25,407 |
| 40 | + | 35,567 | 295,361 | 4,945 | 46,030 | 2,883 | 17,267 | 1,371 | 9,911 | 5,797 | 22,602 |
| 200 | + | 10,177 | 190,701 | 1,777 | 41,800 | 626 | 9,816 | <100 | 1,479 | 3,443 | 23,648 |
| 1,000 | + | 2,422 | 245,683 | 90 | 31,373 | 167 | 13,847 | <100 | 722 | 1,173 | 34,039 |
| 5,000 | + | 1,304 | 35,333 | 91 | 5,228 | <100 | 1,429 | <100 | <100 | 772 | 8,065 |

TABLE 16

Effect of IL-12 on the IgG response to PnPs14 in mice immunized with PnPs14-CRM - conjugate formulated with AlPO

| | | | PnPd14 IgG GMT (fold increase) | | | |
|---|---|---|---|---|---|---|
| Group | IL-12 (ng) | AlPO$_4$ | Week 3 | | Week 5 | |
| P647 | 0 | + | 3,037 | | 27,027 | |
| P648 | 8 | + | 16,681 | (5.5) | 55,855 | (2.1) |
| P649 | 40 | + | 6,667 | (2.2) | 88,271 | (3.4) |
| P650 | 200 | + | 2,333 | (0.8) | 57,076 | (2.1) |
| P651 | 1,000 | + | 611 | (0.2) | 30,886 | (1.1) |
| P652 | 5,000 | + | 617 | (0.2) | 10,989 | (0.4) |

Statistical Comparisons (ANOVA; ∝=0.05)

Week 3 titers

P648 vs P647: significant

P651 vs P547: significant

P649, P650, P652 vs P647: not significant

Week 5 titers

P649 vs P547: significant

P648, P550, P651 vs P647: not significant

TABLE 17

PnPs14 IgG1 titers in mice twice immunized with PnPs14-CRM$_{197}$ conjugate vaccine formulated with or without AlPO$_4$ and various doses of IL-12 Adjuvant Formulation

| Group Code | IL-12 (ng) | AlPO$_4$ | IgG1 GMT (Geometric Mean Titer) |
|---|---|---|---|
| P641 | 0 | – | 9,492 |
| P642 | 8 | – | 5,964 |
| P643 | 40 | – | 14,028 |
| P644 | 200 | – | 4,628 |
| P645 | 1,000 | – | 5,815 |
| P646 | 5,000 | – | 1,757 |
| P647 | 0 | + | 15,283 |
| P648 | 8 | + | 35,730 |
| P649 | 40 | + | 31,855 |
| P650 | 200 | + | 34,166 |
| P651 | 1,000 | + | 15,347 |
| P652 | 5,000 | + | 4,022 |

Statistical Comparisons (ANOVA; α=0.05)

P642, P643, P644, P646, P647, P651 vs P641: not significant

P648, P549, P650 vs P641: significant

P548, P649, P650, P651 vs P547: not significant

P652 vs P647: significant

TABLE 18

PnPs14 IgG2a titers in mice twice immunized with PnPs14-CRM$_{197}$ conjugate vaccine formulated with or without AlPO$_4$ and various doses of IL-12

| Group Code | IL-12 (ng) | AlPO$_4$ | IgG2a GMT at Week 5 (Fold Increase*) |
|---|---|---|---|
| P641 | 0 | – | 97 |
| P642 | 8 | – | 1,418 | (14.6) |
| P643 | 40 | – | 1,509 | (15.6) |
| P644 | 200 | – | 2,228 | (23.0) |
| P645 | 1,000 | – | 4,126 | (42.5) |
| P646 | 5,000 | – | 289 | (3.0) |
| P647 | 0 | + | 806 | |
| P648 | 8 | + | 6,841 | (8.5) |
| P649 | 40 | + | 13,252 | (16.4) |
| P650 | 200 | + | 4,740 | (5.9) |
| P651 | 1,000 | + | 3,291 | (4.1) |
| P652 | 5,000 | + | 368 | (0.5) |

*relative to control vaccines not containing IL-12

Statistical Comparisons (ANOVA; α=0.05)

642, P643, P644, P645 vs P641: significant

P646 vs P641: not significant

648, P649 vs P647: significant

650, P651, P652 vs P647: not significant 643 vs P649: significant

TABLE 19

Anti-CRM$_{197}$ IgG response in Balb/c mice immunized with PnPs14-CRM$_{197}$ conjugate formulated with IL-12 and AlPO$_4$

| Adjuvant | | CRM$_{197}$ IgG Titer (Pooled Sera) | | IgG Subclasses at Week 5 (Pooled Sera) | | |
|---|---|---|---|---|---|---|
| IL-12 (ng) | AlPO$_4$ | Week 3 | Week 5 | IgG1 | IgG2a | IgG2b |
| 0 | – | 3,843 | 8,965 | 703 | 1,269 | 792 |
| 8 | – | 2,456 | 14,389 | 4,674 | <100 | <100 |
| 40 | – | 3,200 | 53,758 | 14,073 | 3,403 | <100 |
| 200 | – | 1,666 | 13,419 | 1,803 | 2,044 | <100 |
| 1,000 | – | 4,999 | 3,663 | <100 | 506 | <100 |
| 5,000 | – | 2,841 | 3,641 | <100 | <100 | <100 |
| 0 | + | 4,870 | 153,075 | 55,922 | 1,796 | 407 |
| 8 | + | 89,558 | 1,515,87 | 377,82 | 85,972 | 10,972 |
| 40 | + | 19,566 | 1,319,10 | 147,03 | 199,29 | 7,206 |
| 200 | + | 6,884 | 315,071 | 48,852 | 35,807 | 3,865 |
| 1,000 | + | 7,292 | 545,827 | 126,72 | 44,190 | 4,127 |
| 5,000 | + | 7,213 | 7,029 | 1,041 | 769 | <100 |

TABLE 20

IgG1 titers to CRM$_{197}$ in Balb/c mice immunized with PnPs14-CRM$_{197}$ conjugate formulated with IL-12 and AlPO$_4$

| Group Code | IL-12 (ng) | AlPO$_4$ | IgG1 GMT | Fold Increase |
|---|---|---|---|---|
| P641 | 0 | – | 317 | — |
| P642 | 8 | – | 1,136 | 3.6 |
| P643 | 40 | – | 9,141 | 28.8 |
| P644 | 200 | – | 1,627 | 5.1 |
| P645 | 1,000 | – | 100 | 0.3 |
| P646 | 5,000 | – | 174 | 0.6 |
| P647 | 0 | + | 22,061 | — |
| P648 | 8 | + | 119,130 | 5.4 |
| P649 | 40 | + | 73,226 | 3.3 |
| P650 | 200 | + | 14,391 | 0.7 |
| P651 | 1,000 | + | 33,468 | 1.5 |
| P652 | 5,000 | + | 317 | 0.01 |

Statistical Comparisons (ANOVA; α=0.05)

P643, P644 vs P641: significant

P642, P645, 5646 vs P641: not significant

648, P649, P650, P651 vs P647: not significant

P642 vs P648, P643 vs P649, P644 vs P650, P645 vs P651: significant

TABLE 21

Cytokine production by splenocytes from mice immunized twice with PnPs14-CRM$_{197}$ formulated with IL-12 in the presence and absence of AlPO$_4$

| Cytokine | Cells Stimulated With | | IL-12 Dose in Vaccine Formulated Without AlPO$_4$ (ng) | | | | | | IL-12 Dose in Vaccine Formulated With AlPO$_4$ (ng) | | | | | |
|---|---|---|---|---|---|---|---|---|---|---|---|---|---|---|
| | Antigen | µg/mL | 0 | 8 | 40 | 200 | 1,000 | 5,000 | 0 | 8 | 40 | 200 | 1,000 | 5,000 |
| IFN-γ | CRM$_{197}$ | 30 | <0.06 | <0.06 | 0.4 | 0.3 | 0.4 | 6.9 | 0.1 | 20.6 | 32.1 | 30.2 | 29.4 | 21.0 |
| (U/mL) | CRM$_{197}$ | 10 | <0.06 | <0.06 | 0.3 | 0.2 | 0.3 | 3.4 | 0.1 | 16.5 | 31.7 | 30.2 | 27.6 | 21.0 |
| | CRM$_{197}$ | 3 | <0.06 | <0.06 | <0.06 | <0.06 | 0.2 | 1.4 | <0.03 | 15.7 | 30.9 | 28.7 | 26.7 | 20.1 |
| | CRM$_{197}$ | 1 | <0.06 | <0.06 | <0.06 | <0.06 | 0.2 | 0.4 | <0.03 | 12.8 | 30.9 | 28.2 | 27.9 | 18.0 |
| | CRM$_{197}$ | 0.3 | <0.06 | <0.06 | <0.06 | <0.06 | 0.1 | 0.1 | <0.03 | 6.3 | 27.5 | 26.2 | 26.5 | 6.5 |
| | Lysozyme | 30 | <0.06 | <0.06 | <0.06 | <0.06 | <0.03 | <0.03 | <0.03 | <0.0 | <0.0 | <0.0 | <0.02 | <0.02 |
| | Con A | 1 | 11.9 | 15.4 | 15.8 | 15.9 | 20.6 | 21.0 | 21.1 | 17.0 | 20.8 | 13.7 | 23.4 | 17.7 |
| | Medium | — | <0.06 | <0.06 | <0.06 | <0.06 | <0.03 | <0.03 | <0.03 | <0.0 | <0.0 | <0.0 | <0.02 | <0.02 |
| IL-5 | CRM$_{197}$ | 30 | 370 | 480 | 2560 | 960 | 60 | 70 | 2010 | 1440 | 5280 | 1640 | 880 | <10 |
| (pg/mL) | CRM$_{197}$ | 10 | 150 | 300 | 1110 | 260 | <24 | <24 | 1220 | 920 | 4590 | 410 | 430 | <10 |
| | CRM$_{197}$ | 3 | 30 | 90 | 910 | 200 | <24 | <24 | 1190 | 690 | 2830 | 1030 | 200 | <10 |
| | CRM$_{197}$ | 1 | <4 | 50 | 200 | 40 | <24 | <24 | 880 | 400 | 2150 | 520 | 140 | <10 |
| | CRM$_{197}$ | 0.3 | <4 | 30 | 70 | <4 | <24 | <24 | 670 | 180 | 440 | 270 | 90 | <10 |
| | Lysozyme | 30 | <4 | <4 | <4 | <4 | <24 | <24 | <24 | <24 | <10 | <10 | <10 | <10 |
| | Con A | 1 | <4 | <4 | <4 | <4 | <24 | <24 | 60 | 80 | 40 | <10 | <10 | <10 |
| | Medium | — | <4 | <4 | <4 | <4 | <24 | <24 | <24 | <24 | <10 | <10 | <10 | <10 |

Example 6

Effect of IL-12/AlPO$_4$ on the Humoral Response to a Nonavalent Pneumococcal Glycoconjugate Vaccine

STUDY DESIGN

Evaluation of the effect of IL-12 on the IgG response to pneumococcal glycoconjugate vaccine was extended to a nonavalent vaccine composed of serotypes 1, 4, 5, 6B, 9V, 14, 18C, 19F, 23F. Swiss Webster mice were immunized with 0.1, 1, or 5 µg of vaccine (carbohydrate weight) at weeks 0 and 3. The vaccine was administered alone, with AlPO$_4$ (100 µg) or with AlPO$_4$ admixed with 50, 200 or 1,000 ng of IL-12. Normal mouse serum was not included in the vaccine. The IgG responses to serotypes 4, 6B, 9V, 14, 18C and to the carrier protein CRM$_{197}$ were evaluated at week 5 (i.e., 2 weeks after boosting by ELISA.

RESULTS

Response to CRM$_{197}$ at Week 5

Addition of IL-12 to a vaccine containing AlPO4 resulted in a dose-dependent increase in IgG2a and IgG2b antibodies to CRM$_{197}$. This was seen at all doses of conjugate tested (Table 22). Increased IgG2a titers were evident in mice receiving 50 ng of the cytokine and were maximal at 1,000 ng. This contrasts with other studies where maximal IgG2a titers were obtained with 40–100 ng of cytokine added to the alum-based vaccine and where higher doses of IL-12 resulted in a diminished immune response. The reason for the differences in dose response between studies is not known. It may relate to differences in the vaccine, i.e., multivalent versus monovalent or that normal mouse serum included in the vaccine in previous studies to stabilize the cytokine at low concentrations was omitted.

Response to Pneumococcal Polysaccharides

Formulating the nonavalent vaccine with AlPO4 enhanced the IgG response to several serotypes including PnPs4, PnPs6B, PnPs9V and PnPs14, especially when the lowest dose of conjugate (0.1 µg) was used (Tables 24–27). Addition of IL-12 did not appear to further enhance the IgG response to these serotypes. In the case of the PnPs18C response, however, addition of 50 or 1,000 ng IL-12 to 5 µg of vaccine containing AlPO4 resulted in higher geometric mean IgG titers to this serotype and higher proportion of mice with PnPs18C IgG titers above 10,000 (Table 23). The responses to PnPs1, 5, 19F and 23F were not evaluated.

Addition OF IL-12 to nonavalent vaccines containing AlPO4 resulted in dose-dependent increases in IgG2a titers to PnPs4, PnPs6B, PnPs9V and PnPs14 (Tables 24–27). Generally, the increase in IgG2a paralleled that for the CRM$_{197}$ response with highest titers being obtained with 1000 ng of IL-12. In contrast to the experiments using monovalent PnPs14 conjugate or bivalent PnPs6B/PnPs14 vaccine, the 50 ng dose of IL-2 had little or no effect on the IgG2a response to these serotypes. The exception is the IgG2a response to PnPs14, as this dose of cytokine appeared, to enhance the response to this serotype (Table 27).

Overall, this study indicates that IL-12 will promote the complement-fixing IgG2a antibody subclass response to multiple pneumococcal serotypes present in a multivalent vaccine.

TABLE 22

Effect of IL-12 on the $CRM_{197}$ response of mice immunized with nonavalent pneumococcal glycoconjugate vaccine formulated with $AlPO_4$

| Vaccine Formulation | | | $CRM_{197}$ Response at Week 5 | | | | |
|---|---|---|---|---|---|---|---|
| Conjugate Dose (μg) | IL-12 (ng) | AlPO4 (μg) | IgG | IgG1 | IgG2a | IgG2b | IgG3 |
| 5.0 | none | none | 391,021 | 138,784 | 1,687 | 3,277 | 102 |
| 5.0 | 0 | 100 | 1,419,910 | 609,704 | 4,328 | 11,349 | 181 |
| 5.0 | 50 | 100 | 3,226,410 | 896,621 | 27,736 | 18,086 | 728 |
| 5.0 | 200 | 100 | 2,991,990 | 584,991 | 87,732 | 28,855 | 2,937 |
| 5.0 | 1,000 | 100 | 16,224,900 | 906,192 | 303,656 | 87,726 | 3,023 |
| 1.0 | none | none | 545,046 | 162,757 | 1,178 | 9,213 | 358 |
| 1.0 | 0 | 100 | 956,584 | 338,751 | 1,284 | 4,118 | 306 |
| 1.0 | 50 | 100 | 1,936,170 | 370,961 | 6,677 | 31,982 | 931 |
| 1.0 | 200 | 100 | 4,788,500 | 660,082 | 187,034 | 36,785 | 1,065 |
| 1.0 | 1,000 | 100 | 12,404,500 | 644,151 | 533,065 | 69,185 | 1,176 |
| 0.1 | none | none | 18,215 | 3,800 | <100 | <100 | <100 |
| 0.1 | 0 | 100 | 561,952 | 157,362 | 1,437 | 7,744 | <100 |
| 0.1 | 50 | 100 | 807,363 | 141,670 | 15,064 | 25,978 | 2,092 |
| 0.1 | 200 | 100 | 1,560,380 | 313,263 | 38.686 | 51.737 | 306 |
| 0.1 | 1,000 | 100 | 2,296,310 | 202,111 | 112,158 | 36,958 | 1,054 |

Mice were immunized with indicated dose of nonavalent pneumococcal glycoconjugate vaccine at weeks 0 and 3. The conjugates were formulated alone, with AlPO (100 μg) or with $AlPO_4$ plus IL-12. Sera from the week 5 bleed were analyzed for IgG antibodies to $CRM_{197}$.

TABLE 23

Effect of IL-12 on the response to PnPs18C in mice immunized with 5 μg nonavalent pneumococcal glycoconjugate vaccine formulated with AlPO4

| Vaccine Formulation | | | PnPs18C Response | |
|---|---|---|---|---|
| Conjugate Dose (μg) | IL-12 (ng) | $AlPO_4$ (μg) | IgG Titer (GMT) | Mice With Titer >10,000 (n = 5) |
| 5 | 0 | 0 | 2,933 | 1 |
| 5 | 50 | 100 | 23,725 | 4 |
| 5 | 1,000 | 100 | 48,375 | 5 |

Mice were immunized with indicated dose of nonavalent pneumococcal glycoconjugate vaccine at weeks 0 and 3. The conjugates were formulated alone, with $AlPO_4$ (100 μg) or with $AlPO_4$ plus IL-12. Individual mouse Sera from the week 5 bleed were analyzed for IgG antibodies to PnPs18C.

TABLE 24

Effect of IL-12 on the PnPs4 response of mice immunized with nonavalent pneumococcal glycoconjugate vaccine formulated with AlPO4

| Vaccine Formulation | | | PnPs4 Response at Week 5 | | | | |
|---|---|---|---|---|---|---|---|
| Conjugate Dose (μg) | IL-12 (ng) | $AlPO_4$ (μg) | IgG | IgG1 | IgG2a | IgG2b | IgG3 |
| 5.0 | none | none | 55,068 | 13,731 | <500 | <500 | <500 |
| 5.0 | 0 | 100 | 233,008 | 55,620 | <500 | 1,157 | 990 |
| 5.0 | 50 | 100 | 285,806 | 64,493 | 1,050 | 1,329 | 2,634 |
| 5.0 | 200 | 100 | 203,236 | 56,654 | 1,789 | 692 | 2,693 |
| 5.0 | 1,000 | 100 | 371,329 | 35,778 | 4,048 | 1,080 | 3,820 |
| 1.0 | none | none | 77,714 | 9,070 | <500 | 608 | <500 |
| 1.0 | 0 | 100 | 141,371 | 14,829 | <500 | <500 | 542 |
| 1.0 | 50 | 100 | 97,999 | 14,336 | 449 | 814 | 1,034 |
| 1.0 | 200 | 100 | 137,674 | 17,380 | 752 | 569 | 816 |
| 1.0 | 1,000 | 100 | 214,739 | 25,056 | 4,685 | 1,260 | 4,055 |
| 0.1 | none | none | 4,726 | 706 | <500 | <500 | <500 |
| 0.1 | 0 | 100 | 79,686 | 12,071 | <500 | 869 | <500 |
| 0.1 | 50 | 100 | 70,917 | 9,649 | 1,032 | 1,389 | <500 |
| 0.1 | 200 | 100 | 46,503 | 7,779 | 885 | 1,056 | 572 |
| 0.1 | 1,000 | 100 | 87,762 | 6,788 | 1,725 | <500 | 1,682 |

Mice were immunized with indicated dose of nonavalent pneumococcal glycoconjugate vaccine at weeks 0 and 3. The conjugates were formulated alone, with AlPO4 (100 μg) or with AlPO4 plus IL-12. Individual mouse Sera from the week 5 bleed were analyzed for IgG antibodies to PnPs4.

TABLE 25

Effect of IL-12 on the PnPs6B response of mice immunized with nonavalent pneumococcal glycoconjugate vaccine formulated with AlPO4

| Vaccine Formulation | | | PnPs6B Response at Week 5 | | | | |
|---|---|---|---|---|---|---|---|
| Conjugate Dose (μg) | IL-12 (ng) | $AlPO_4$ (μg) | Total IgG | IgG1 | IgG2a | IgG2b | IgG3 |
| 5.0 | none | none | 64,734 | 20,221 | <100 | 195 | 325 |
| 5.0 | 0 | 100 | 103,686 | 39,061 | 138 | 2,498 | 1,801 |
| 5.0 | 50 | 100 | 487,798 | 127,753 | 916 | 3,200 | 13,758 |
| 5.0 | 200 | 100 | 214,743 | 59,979 | 924 | 959 | 6,459 |
| 5.0 | 1,000 | 100 | 427,514 | 94,478 | 4,426 | 2,552 | 13,142 |
| 1.0 | none | none | 165,558 | 37,646 | <100 | 2,047 | 2,337 |

TABLE 25-continued

Effect of IL-12 on the PnPs6B response of mice immunized with nonavalent pneumococcal glycoconjugate vaccine formulated with AlPO4

| Vaccine Formulation | | | | | | | |
|---|---|---|---|---|---|---|---|
| Conjugate | | | PnPs6B Response at Week 5 | | | | |
| Dose (μg) | IL-12 (ng) | AlPO₄ (μg) | Total IgG | IgG1 | IgG2a | IgG2b | IgG3 |
| 1.0 | 0 | 100 | 730,910 | 133,441 | 990 | 2,770 | 7,468 |
| 1.0 | 50 | 100 | 428,549 | 77,124 | 838 | 3,755 | 12,931 |
| 1.0 | 200 | 100 | 164,820 | 29,685 | 316 | 662 | 4,703 |
| 1.0 | 1,000 | 100 | 401,513 | 51,132 | 11,442 | 2,735 | 31,613 |
| 0.1 | none | none | 4,787 | 1,034 | <100 | <100 | <100 |
| 0.1 | 0 | 100 | 370,177 | 71,287 | 603 | 11,372 | 5,712 |
| 0.1 | 50 | 100 | 137,091 | 25,447 | 1,029 | 3,346 | 3,411 |
| 0.1 | 200 | 100 | 128,428 | 31,634 | 434 | 2,698 | 1,891 |
| 0.1 | 1,000 | 100 | 524,385 | 67,301 | 9,611 | 11,587 | 8,711 |

Mice were immunized with indicated dose of nonavalent pneumococcal glycoconjugate vaccine at weeks 0 and 3. The conjugates were formulated alone, with AlPO4 (100 μg) or with AlPO4 plus IL-12. Sera from the week 5 bleed were analyzed for IgG antibodies to PnPs6B.

TABLE 26

Effect of IL-12 on the PnPs9V response of mice immunized with nonavalent pneumococcal glycoconjugate vaccine formulated with AlPO4

| Vaccine Formulation | | | PnPs9V Response at Week 5 | | | | |
|---|---|---|---|---|---|---|---|
| Conjugate Dose (μg) | IL-12 (ng) | AlPO₄ (μg) | Total IgG | IgG1 | IgG2a | IgG2b | IgG3 |
| 5.0 | none | none | 36,831 | 15,568 | 306 | 250 | 317 |
| 5.0 | 0 | 100 | 78,614 | 37,544 | 359 | 667 | 286 |
| 5.0 | 50 | 100 | 117,345 | 61,031 | 1,073 | 834 | 2,089 |
| 5.0 | 200 | 100 | 134,333 | 35,031 | 2,973 | 748 | 2,594 |
| 5.0 | 1,000 | 100 | 197,407 | 40,368 | 15,353 | 2,147 | 1,945 |
| 1.0 | none | none | 81,932 | 34,845 | 546 | 2,232 | 735 |
| 1.0 | 0 | 100 | 100,448 | 55,608 | 660 | 1,274 | 699 |
| 1.0 | 50 | 100 | 157,316 | 47,285 | 1,084 | 2,036 | 4,730 |
| 1.0 | 200 | 100 | 154,672 | 48,318 | 1,765 | 860 | 2,044 |
| 1.0 | 1,000 | 100 | 168,614 | 54,223 | 10,037 | 1,469 | 3,006 |
| 0.1 | none | none | <500 | 181 | <100 | <100 | <100 |
| 0.1 | 0 | 100 | 86,952 | 26,425 | 206 | 485 | 1,285 |
| 0.1 | 50 | 100 | 20,746 | 6,381 | 579 | 726 | 353 |
| 0.1 | 200 | 100 | 19,966 | 5,501 | 778 | 325 | 235 |
| 0.1 | 1,000 | 100 | 50,219 | 3,511 | 1,290 | 1,036 | 714 |

Mice were immunized with indicated dose of nonavalent pneumococcal glycoconjugate vaccine at weeks 0 and 3. The conjugates were formulated alone, with AlPO4 (100 μg) or with AlPO4 plus IL-12. Sera from the week 5 bleed were analyzed for IgG antibodies to PnPs9V.

TABLE 27

Effect of IL-12 on the PnPs14 response of mice immunized with nonavalent pneumococcal glyconconjugate vaccine formulated with AlPO4

| Vaccine Formulation | | | | | | | |
|---|---|---|---|---|---|---|---|
| Conjugate | | | PnPs14 Response at Week 5 | | | | |
| Dose (μg) | IL-12 (ng) | AlPO₄ (μg) | Total IgG | IgG1 | IgG2a | IgG2b | IgG3 |
| 5.0 | none | none | 2,676 | 1,750 | <100 | <100 | <100 |
| 5.0 | 0 | 100 | 11,792 | 15,704 | 124 | 580 | 1,723 |
| 5.0 | 50 | 100 | 56,712 | 31,056 | 6,144 | 2,854 | 11,840 |
| 5.0 | 200 | 100 | 5,049 | 3,050 | 1,588 | <100 | 2,106 |
| 5.0 | 1,000 | 100 | 11,848 | 3,760 | 1,853 | 366 | 2,035 |
| 1.0 | none | none | 4,846 | 3,116 | <100 | 409 | 699 |
| 1.0 | 0 | 100 | 20,605 | 31,022 | 291 | 2,383 | 9,286 |
| 1.0 | 50 | 100 | 8,338 | 4,722 | 1,354 | 715 | 10,079 |
| 1.0 | 200 | 100 | 5,618 | 3,252 | 1,014 | <100 | 583 |
| 1.0 | 1,000 | 100 | 13,026 | 3,551 | 2,879 | 671 | 2,070 |
| 0.1 | none | none | <100 | 105 | <100 | <100 | <100 |
| 0.1 | 0 | 100 | 114 | 392 | <100 | <100 | 710 |
| 0.1 | 50 | 100 | 2,140 | 2,838 | <100 | 245 | 3,592 |
| 0.1 | 200 | 100 | 2,200 | 426 | <100 | 622 | 759 |
| 0.1 | 1,000 | 100 | 394 | 378 | 219 | 100 | 658 |

Mice were immunized with indicated dose of nonavalent pneumococcal glycoconjugate vaccine at weeks 0 and 3. The conjugates were formulated alone, with AlPO4 (100 μg) or with AlPO4 plus IL-12. Sera from the week 5 bleed were analyzed for IgG antibodies to PnPs14.

Example 7

The Effect of IL-12 and AlPO4 on the Immune Response to *Neiserria meningitidis* Type C (menC) Glyconconjugate Vaccine

STUDY DESIGN

This study evaluated IL-12 with a vaccine against *Neiserria meningitidis* type C (menC). Swiss Webster mice were immunized at weeks 0 and 3 with 0.1 μg or 1 μg of MenC glycoconjugate formulated alone, with AlPO₄ (100 μg) or a combination of IL-12 (50 ng) and AlPO4. Normal mouse serum was not added to the vaccine. Mice were bled at weeks 3 and 5 and sera analyzed for IgG antibodies to menC polysaccharide by ELISA.

RESULTS

When immunized with the higher dose of conjugate, equivalent *menC* IgG titers were generated regardless of the adjuvant formulation. The addition of IL-12/AlPO4 to the vaccine, however, resulted in higher IgG2a titers to the polysaccharide than if formulated with AlPO4 (but no IL-12) or no adjuvant.

In mice immunized with the lower dose of conjugate, higher mening C titers were obtained when the vaccine was formulated with AlPO4 (Table 28). The addition of IL-12 to the adjuvant did not enhance the overall IgG titer but did result in a >10-fold increase in IgG2a antibodies. These data show that IL-12 in combination with AlPO4 can promote the induction of complement-fixing IgG subclasses to menC glyconconjugate vaccine.

TABLE 28

Effect of IL-12/AlPO4 on the IgG response to menC glyconconjugate vaccine

| Vaccine Formulation | | | MenC Response | | | | | |
|---|---|---|---|---|---|---|---|---|
| MenC Conjugate | IL-12 | AlPO$_4$ | IgG | | IgG Subclass at Week 5 | | | |
| ($\mu$g) | (ng) | ($\mu$g) | Week 3 | Week 5 | IgG1 | IgG2a | IgG2b | IgG3 |
| 1.0 | 50 | 100 | 33,176 | 598,027 | 83,662 | 7,218 | 4,351 | 1,436 |
|  | 0 | 100 | 34,553 | 404,111 | 71,017 | 1,383 | 3,085 | 1,006 |
|  | 0 | 0 | 16,254 | 288,493 | 63,043 | 1,965 | <100 | 502 |
| 0.1 | 50 | 100 | 2,584 | 68,678 | 9,604 | 3,440 | 1,967 | 512 |
|  | 0 | 100 | 8,174 | 30,450 | 6,532 | 288 | 429 | <100 |
|  | 0 | 0 | 1,724 | 7,894 | 1,767 | <100 | <100 | <100 |

Example 8

The Effect of IL-12 and AlPO4 on the Immune Response to *Hemophilus influenzae* Type b Glycoconjugate Vaccine (HbOC)

STUDY DESIGN

This study evaluated IL-12 with a vaccine against *Hemophilus influenzae* type b. Swiss Webster mice (10 per group) were immunized at weeks 0 and 3 with 0.1 $\mu$g or 1.0 $\mu$g of glycoconjugate vaccine consisting of capsular polysaccharide from *Hemophilus influenzae* type b (HibPs) conjugated to CRM$_{197}$. The vaccine (HbOC) was administered alone or in combination with AlPO4 (100 $\mu$g) or a mixture of IL-12 (50 ng) plus AlPO4. Normal mouse serum was not added to the vaccine. The mice were bled at weeks 3 and 5. The antibody response to HibPs was measured using a Farr assay which measures all antibodies binding to the saccharide regardless of isotype, i.e., IgM, IgG and IgA. The IgG subclass response was measured by ELISA. Additionally, the IgG and IgG subclass response to CRM$_{197}$ was also determined by ELISA.

RESULTS

The titers of anti-HibPs antibodies in serum pooled from the week 3 bleed (primary response) were not different between mice immunized with vaccine formulated alone, with AlPO4 or IL-12 plus AlPO4 regardless of the dose of conjugate used for immunization (Table 29). Analysis of pooled serum from the week 5 bleed suggested that in mice immunized with 1 $\mu$g of HbOC with IL-12 plus alum resulted in at least a 10-fold higher anti-HibPs than when given with alum or without adjuvant (Table 30) However, analysis of individual mouse sera showed that this was due to a single mouse having a titer of approximately 10,000 $\mu$g/mL. When the results are expressed as geometric mean titer there was no evidence of an enhanced HibPs response due to IL-12. The IgG subclass response to HibPs was evaluated on pooled sera by ELISA The combination of IL-12 and AlPO4 appeared to enhance the IgG2a titer 3-fold in mice immunized with 1 $\mu$g of conjugate. However, this was no different than the titer obtained with vaccine adjuvanted with AlPO4 alone. In mice immunized with 0.1 $\mu$g of HbOC, IL-12 plus AlPO4 did not enhance the IgG2a titer to HibPs. That the IL-12/AlPO4 adjuvant combination was active was revealed by analysis of the anti-CRM$_{197}$ response (Table 31) where increased IgG2a titer to the carrier protein was seen in mice immunized with either dose of conjugate.

TABLE 29

Anti-HibPs antibody response of mice immunized with HbOC formulated with IL-12 and AlPO4

| Vaccine Formulation | | | Anti-HibPs Antibody Response ($\mu$g/mL) | | |
|---|---|---|---|---|---|
| | | | Week 3 | Week 5 | |
| HbOC ($\mu$g) | IL-12 (ng) | AlPO$_4$ ($\mu$g) | Pooled Serum | Pooled Serum | GMT* |
| 1.0 | 50 | 100 | 9.73 | 469.16 | 26.92 |
|  | 0 | 100 | 13.04 | 42.55 | 21.30 |
|  | 0 | 0 | 5.12 | 33.19 | 2.25 |
| 0.1 | 50 | 100 | 3.18 | 30.95 | ND |
|  | 0 | 100 | 4.06 | 15.11 | ND |
|  | 0 | 0 | 3.03 | 14.05 | ND |

TABLE 30

Effect of IL-12 and AlPO4 on the IgG subclass response to HbOC

| Vaccine Formulation | | | Anti-HibPs IgG Subclass Response at Week 5 (ELISA Endpoint Titer) | |
|---|---|---|---|---|
| HbOC ($\mu$g) | IL-12 (ng) | AlPO$_4$ ($\mu$g) | IgG1 | IgG2a |
| 1.0 | 50 | 100 | 754,745 | 26,899 |
|  | 0 | 100 | 122,637 | 12,880 |
|  | 0 | 0 | 73,114 | 8,570 |
| 0.1 | 50 | 100 | 46,673 | 17,290 |
|  | 0 | 100 | 68,176 | 14,971 |
|  | 0 | 0 | 35,237 | 11,418 |

TABLE 31

Anti-CRM$_{197}$ IgG response of mice immunized with HbOC formulated with IL-12 and AlPO4

| Vaccine Formulation | | | Anti-CRM$_{197}$ Response at Week 5 | | | |
|---|---|---|---|---|---|---|
| HbOC ($\mu$g) | IL-12 (ng) | AlPO$_4$ ($\mu$g) | IgG | IgG1 | IgG2a | IgG2b |
| 1.0 | 50 | 100 | 1,775,700 | 681,944 | 39,672 | 40,527 |
|  | 0 | 100 | 2,221,780 | 818,557 | 19,010 | 32,672 |
|  | 0 | 0 | 3,979,530 | 1,466,010 | 8,059 | 15,961 |

TABLE 31-continued

Anti-CRM$_{197}$ IgG response of mice immunized with HbOC formulated with IL-12 and AlPO4

| Vaccine Formulation | | | Anti-CRM$_{197}$ Response at Week 5 | | | |
|---|---|---|---|---|---|---|
| HbOC (µg) | IL-12 (ng) | AlPO$_4$ (µg) | IgG | IgG1 | IgG2a | IgG2b |
| 0.1 | 50 | 100 | 761,027 | 292,448 | 38,258 | 21,008 |
|  | 0 | 100 | 891,251 | 346,728 | 6,546 | 14,832 |
|  | 0 | 0 | 874,805 | 151,397 | 1,899 | 3,517 |

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a mixture of a pneumococcal capsular polysaccharide, an adjuvant amount of interleukin-12 and an aqueous suspension of alum, and optionally comprising a physiologically acceptable vehicle.

2. A composition according to claim 1, wherein the interleukin-12 is adsorbed onto the alum suspension.

3. A composition according to claim 1, wherein the interleukin-12 is human interleukin-12.

4. A composition according to claim 1, wherein the alum is aluminum hydroxide or aluminum phosphate.

5. A composition according to claim 1, wherein the pneumococcal capsular polysaccharide is selected from the group consisting of pneumococcal capsular polysaccharide serotypes 1, 4, 5, 6B, 9V, 14, 18C, 19F and 23F and combinations thereof.

6. A composition according to claim 1, wherein the pneumococcal capsular polysaccharide is conjugated to a carrier molecule.

7. A composition according to claim 6, wherein the carrier molecule is selected from the group consisting of tetanus toxin, diphtheria toxin, pertussis toxin and non-toxic variants thereof.

8. A composition according to claim 7, wherein the carrier molecule is CRM$_{197}$.

9. A method of eliciting an immune response to a pneumococcal capsular polysaccharide, comprising administering to a mammalian host an effective amount of a vaccine composition comprising a mixture of a pneumococcal capsular polysaccharide, an adjuvant amount of interleukin-12 and an aqueous suspension of alum, and optionally comprising a physiologically acceptable vehicle.

10. A method according to claim 9, wherein the interleukin-12 is adsorbed onto the alum suspension.

11. A method according to claim 9, wherein the interleukin-12 is human interleukin-12.

12. A method according to claim 9, wherein the alum is aluminum hydroxide or aluminum phosphate.

13. A method according to claim 9, wherein the pneumococcal capsular polysaccharide is selected from the group consisting of pneumococcal capsular polysaccharide serotypes 1, 4, 5, 6B, 9V, 14, 18C, 19F and 23F and combinations thereof.

14. A method according to claim 9, wherein the pneumococcal capsular polysaccharide is conjugated to a carrier molecule.

15. A method according to claim 14, wherein the carrier molecule is selected from the group consisting of tetanus toxin, diphtheria toxin, pertussis toxin and non-toxic variants thereof.

16. A method according to claim 15, wherein the carrier molecule is CRM$_{197}$.

17. An immunogenic composition comprising a mixture of a pneumococcal capsular polysaccharide, an adjuvant amount of interleukin-12 and an aqueous suspension of alum, and optionally comprising a physiologically acceptable vehicle.

18. An immunogenic composition according to claim 17, wherein the interleukin-12 is adsorbed onto the alum suspension.

19. An immunogenic composition according to claim 17, wherein the interleukin-12 is human interleukin-12.

20. An immunogenic composition according to claim 17, wherein the alum is aluminum hydroxide or aluminum phosphate.

21. An immunogenic composition according to claim 17, wherein the pneumococcal capsular polysaccharide is selected from the group consisting of pneumococcal capsular polysaccharide serotypes 1, 4, 5, 6B, 9V, 14, 18C, 19F and 23F and combinations thereof.

22. An immunogenic composition according to claim 17, wherein the pneumococcal capsular polysaccharide is conjugated to a carrier molecule.

23. An immunogenic composition according to claim 22, wherein the carrier molecule is selected from the group consisting of tetanus toxin, diphtheria toxin, pertussis toxin and non-toxic variants thereof.

24. An immunogenic composition according to claim 23, wherein the carrier molecule is CRM$_{197}$.

* * * * *